US011850059B1

(12) United States Patent
Lee et al.

(10) Patent No.: US 11,850,059 B1
(45) Date of Patent: Dec. 26, 2023

(54) TECHNIQUE FOR IDENTIFYING COGNITIVE FUNCTION STATE OF USER

(71) Applicant: HAII corp., Seoul (KR)

(72) Inventors: Jee Hang Lee, Goyang-si (KR); Ho Yung Kim, Seoul (KR); Dong Han Kim, Seoul (KR); Hye Bin Hwang, Incheon (KR); Chan Yeong Park, Seoul (KR); Ji An Choi, Seoul (KR); Hyun Jeong Ko, Seoul (KR); Su Yeon Park, Seoul (KR); Byung Hun Yun, Seoul (KR)

(73) Assignee: HAII CORP., Seoul (KR)

( * ) Notice: Subject to any disclaimer, the term of this patent is extended or adjusted under 35 U.S.C. 154(b) by 0 days.

(21) Appl. No.: 18/322,427

(22) Filed: May 23, 2023

(30) Foreign Application Priority Data

Jun. 10, 2022 (KR) .................. 10-2022-0070491
Sep. 13, 2022 (KR) .................. 10-2022-0114972

(51) Int. Cl.
*A61B 5/00* (2006.01)
*G10L 15/02* (2006.01)
*G10L 15/04* (2013.01)
*G10L 15/22* (2006.01)
*G10L 15/26* (2006.01)
*G10L 25/66* (2013.01)

(52) U.S. Cl.
CPC .......... *A61B 5/4088* (2013.01); *A61B 5/4803* (2013.01); *G10L 15/02* (2013.01); *G10L 15/04* (2013.01); *G10L 15/22* (2013.01); *G10L 15/26* (2013.01); *G10L 25/66* (2013.01)

(58) Field of Classification Search
CPC ................... A61B 5/4088; A61B 5/4803
See application file for complete search history.

(56) References Cited

U.S. PATENT DOCUMENTS

| 10,213,149 B2* | 2/2019 | Lee ................. G16H 50/20 |
| 2004/0209810 A1* | 10/2004 | Gill ................. A61K 38/185 514/8.4 |
| 2012/0214143 A1* | 8/2012 | Severson ............... G16H 50/30 434/236 |
| 2014/0199670 A1* | 7/2014 | Stack ................. G09B 7/00 434/236 |
| 2015/0112899 A1* | 4/2015 | Dagum ................. A61B 5/163 706/12 |
| 2017/0097929 A1* | 4/2017 | Cecchi ................. G06F 16/35 |
| 2019/0113973 A1* | 4/2019 | Coleman ................. G06F 3/011 |
| 2020/0219295 A1* | 7/2020 | el Kaliouby ............ G06T 11/00 |

(Continued)

FOREIGN PATENT DOCUMENTS

| CN | 114429817 A | * | 5/2022 | ............ G16H 50/30 |
| JP | 2018015139 A | | 2/2018 | |

(Continued)

*Primary Examiner* — Daniel C Washburn
*Assistant Examiner* — Oluwadamilola M Ogunbiyi
(74) *Attorney, Agent, or Firm* — Umberg Zipser LLP

(57) ABSTRACT

Disclosed is a method of identifying, by at least one processor of a device, a cognitive function state of a user. The method may include inputting user information, at least one voice data, and speech time information related to the at least one voice data to a cognitive function state identification model, and identifying a cognitive function state of the user based on first output data that is output by the cognitive function state identification model.

15 Claims, 13 Drawing Sheets

(56) References Cited

U.S. PATENT DOCUMENTS

| | | | | |
|---|---|---|---|---|
| 2020/0245949 | A1* | 8/2020 | Dagum | G16H 50/30 |
| 2020/0321124 | A1* | 10/2020 | Ford | G06N 20/20 |
| 2021/0270848 | A1* | 9/2021 | Mukaetova-Ladinska | A61K 31/27 |
| 2021/0353218 | A1* | 11/2021 | Edwards | G10L 25/66 |
| 2021/0393955 | A1* | 12/2021 | Hagedorn | A61B 5/291 |
| 2022/0076694 | A1* | 3/2022 | Pijl | G16H 40/67 |
| 2022/0285027 | A1* | 9/2022 | Gossens | G06N 20/10 |
| 2023/0215153 | A1* | 7/2023 | Kasischke | G06T 7/0012 382/131 |
| 2023/0314452 | A1* | 10/2023 | Kastner | G01N 33/6896 435/7.1 |

FOREIGN PATENT DOCUMENTS

| | | | | |
|---|---|---|---|---|
| KR | 1020170028295 A | | 3/2017 | |
| KR | 1020190135908 A | | 12/2019 | |
| KR | 20200128555 A | * | 11/2020 | G16H 50/30 |
| KR | 1020210017616 A | | 2/2021 | |
| KR | 102257291 B1 | | 5/2021 | |
| KR | 102314213 B1 | | 10/2021 | |
| KR | 102321197 B1 | | 11/2021 | |
| KR | 1020210155335 A | | 12/2021 | |
| WO | WO-2022086454 A1 | * | 4/2022 | A61B 5/0077 |
| WO | WO-2022212740 A2 | * | 10/2022 | G16H 50/20 |

\* cited by examiner

Fig. 4

| Story title | Number of images |
|---|---|
| Rabbit and Turtle | 4 |
| Kongjwi Patjwi | 4 |
| Sun and Moon | 4 |
| Heungbu and Nolbu | 5 |

TECHNIQUE FOR IDENTIFYING COGNITIVE FUNCTION STATE OF USER

BACKGROUND

1. Technical Field

The present disclosure relates to a technique for identifying a cognitive function state of a user and, particularly, to a device and method for identifying a cognitive function state of a user based on user information, at least one voice data, and speech time information related to the at least one voice data.

2. Related Art

Alzheimer's disease (AD), which is a brain disease caused by aging, causes progressive memory impairment, cognitive deficits, changes in individual personality, etc. In addition, dementia refers to a state of persistent and overall cognitive function decline that occurs when a person who has led a normal life suffers from damage to brain function due to various causes. In this case, cognitive function refers to various intellectual abilities, such as memory, language ability, temporal and spatial understanding ability, judgment ability, and abstract thinking ability. Each cognitive function is closely related to a specific part of the brain. The most common form of dementia is Alzheimer's disease.

Various methods have been proposed for diagnosing Alzheimer's disease, dementia, or mild cognitive impairment. For example, a method of diagnosing Alzheimer's disease or mild cognitive impairment using the expression level of miR-206 in the olfactory tissue, and a method for diagnosing dementia using a biomarker that characteristically increases in blood are known.

However, since special equipment or tests necessary for biopsy are required so as to use miR-206 in the olfactory tissue, and blood from a patient should be collected by an invasive method so as to use biomarkers in blood, there is a disadvantage that the patient's rejection feeling is relatively large.

Therefore, there is an urgent need to develop a method capable of diagnosing a user's cognitive function state in a way in which the patient hardly feels a sense of rejection without any special equipment or examination.

SUMMARY

The present disclosure has been made in view of the above problems, and it is one object of the present disclosure to provide an accurate cognitive function state diagnosis method where patients hardly feel rejection.

It will be understood that technical problems of the present disclosure are not limited to the aforementioned problem and other technical problems not referred to herein will be clearly understood by those skilled in the art from the description below.

In an embodiment, a method of identifying, by at least one processor of a device, a cognitive function state of a user, may include inputting user information, at least one voice data, and speech time information related to the at least one voice data to a cognitive function state identification model, and identifying a cognitive function state of the user based on first output data that is output by the cognitive function state identification model.

According to some embodiments of the present disclosure, the first output data may include at least one of a cognitive function state value related to the cognitive function state of the user and a predicted score value that is obtained by predicting a score which is able to obtained when the user performs a cognitive ability test.

According to some embodiments of the present disclosure, the identifying of the cognitive function state of the user based on the first output data that is output by the cognitive function state identification model may include determining the cognitive function state of the user based on the cognitive state identification value, and determining the intensity of the cognitive function state of the user based on the predicted score value.

According to some embodiments of the present disclosure, the cognitive function state identification model may include a converter configured to convert the at least one voice data into text data based on the at least one voice data and the speech time information, a first model configured to generate second output data based on the text data, a logic-based event processor configured to extract linguistic feature information and voice feature information based on the second output data, and at least one model configured to generate the first output data, based on the linguistic feature information, the voice feature information, and the user information.

According to some embodiments of the present disclosure, the second output data may include word segment information, rhythmical information, interjection information, and syllable unit voice data.

According to some embodiments of the present disclosure, the word segment information may include information on at least one word included in the text data and information on a time when the at least one word is spoken.

According to some embodiments of the present disclosure, the rhythmical information may include information related to at least one of a strength and weakness of a sound, a rhythm of the sound, and a high and low of the sound when the user speaks the at least one word.

According to some embodiments of the present disclosure, the interjection information may include information on a type of each of one or more interjections included in the text data, a speech time of each of the one or more interjections, a number of repetitions of each of the one or more interjections, and a total repetition time of each of the one or more interjections.

According to some embodiments of the present disclosure, the linguistic feature information may include information on frequency of use of the at least one interjection and information relating to whether a preset word is included in the at least one voice data.

According to some embodiments of the present disclosure, the voice feature information may include at least one of information on a total speech time that is taken when the user speaks, information on frequency that the user pauses while speaking compared to the total speech time, and information on a total time for which the user pauses while speaking compared to the total speech time.

According to some embodiments of the present disclosure, the at least one voice data may be obtained by using at least one of a method of obtaining first voice data and a method of obtaining second voice data, which is different from the method of obtaining the first voice data.

According to some embodiments of the present disclosure, the method of obtaining the first voice data may include performing a first task for obtaining a plurality of first voice data related to a plurality of images related to one story, respectively, while operating in conjunction with causing the plurality of images to be sequentially displayed in a user terminal one by one, and performing a second task for obtaining the second voice data while operating in conjunction with causing information on the one story to be displayed in the user terminal without displaying an image.

According to some embodiments of the present disclosure, the method of obtaining the second voice data may include performing a third task for causing a user terminal to display a first screen including a sentence, performing a fourth task for causing the user terminal to obtain an image including the user's eyes while operating in conjunction with displaying a moving object instead of the first screen, and performing a fifth task for causing the user terminal to obtain a recording file including the at least one voice data while operating in conjunction with displaying a second screen on which the sentence is hidden.

According to some embodiments of the present disclosure, the user information may include at least one of information on an age and sex of the user and cognitive test result data of the user.

In another embodiment, a computer program stored in a computer-readable storage medium may perform steps of identifying a cognitive function state of a user, when being executed by at least one processor of a device. The steps may include inputting user information, at least one voice data, and speech time information related to the at least one voice data to a cognitive function state identification model, and identifying a cognitive function state of the user based on first output data that is output by the cognitive function state identification model.

According to some embodiments of the present disclosure, a device for identifying a cognitive function state of a user may include a storage unit configured to store at least one program instruction and at least one processor configured to perform the at least one program instruction. The at least one processor may input user information, at least one voice data, and speech time information related to the at least one voice data to a cognitive function state identification model, and may identify a cognitive function state of the user based on first output data that is output by the cognitive function state identification model.

The technical solutions obtainable in the present disclosure are not limited to the above-mentioned solutions, other solutions not mentioned will be clearly understood by those skilled in the art from the description below.

The effect of the technique for identifying the user's cognitive function state according to the present disclosure will be described.

According to some embodiments of the present disclosure, the user's cognitive function state can be accurately diagnosed in a way in which the user hardly feels objection.

It will be understood that effects obtained by the present disclosure are not limited to the aforementioned effect and other effects not referred to herein will be clearly understood by those skilled in the art from the description below.

BRIEF DESCRIPTION OF THE DRAWINGS

Various embodiments of the present disclosure are described with reference to the accompanying drawings. In this case, like reference numbers are used to refer to like elements. In the following embodiments, numerous specific details are set forth so as to provide a thorough understanding of one or more embodiments for purposes of explanation. It will be apparent, however, that such embodiment(s) may be practiced without these specific details.

FIGS. 3 to 5 are diagrams for describing an example of a method of obtaining at least one voice data according to some embodiments of the present disclosure.

DETAILED DESCRIPTION

Figure 1:
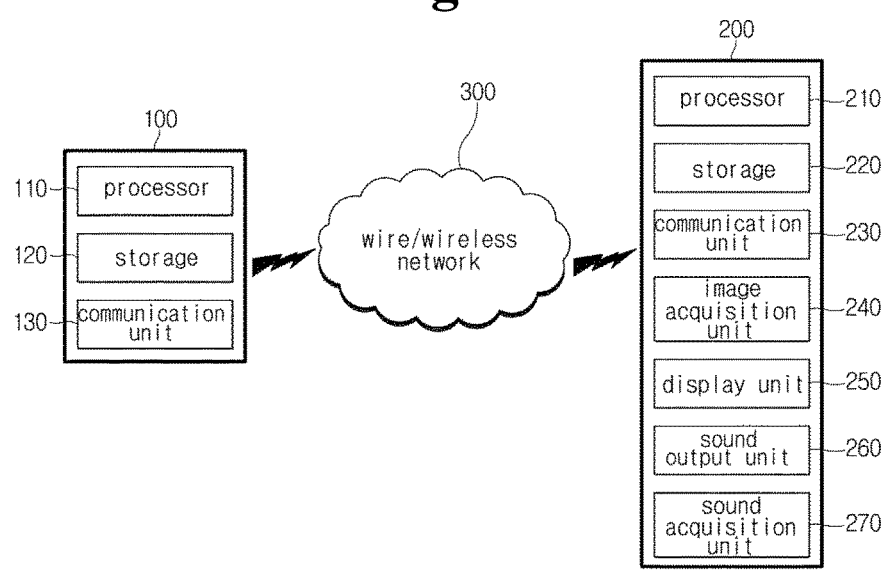
FIG. 1 is a schematic diagram for explaining a system for identifying a user's cognitive function state according to some embodiments of the present disclosure.

Hereinafter, various embodiments of an apparatus according to the present disclosure and a method of controlling the same will be described in detail with reference to the accompanying drawings. Regardless of the reference numerals, the same or similar components are assigned the same reference numerals, and overlapping descriptions thereof will be omitted.

Objectives and effects of the present disclosure, and technical configurations for achieving the objectives and the effects will become apparent with reference to embodiments described below in detail in conjunction with the accompanying drawings. In describing one or more embodiments of the present disclosure, a detailed description of known functions and configurations incorporated herein will be omitted when it may make the subject matter of the present disclosure unclear.

The terms used in the specification are defined in consideration of functions used in the present disclosure, and can be changed according to the intent or conventionally used methods of clients, operators, and users. The features of the present disclosure will be more clearly understood from the accompanying drawings and should not be limited by the accompanying drawings, and it is to be appreciated that all changes, equivalents, and substitutes that do not depart from the spirit and technical scope of the present disclosure are encompassed in the present disclosure.

The suffixes "module" and "unit" of elements herein are used for convenience of description and thus can be used interchangeably and do not have any distinguishable meanings or functions.

Terms including an ordinal number, such as first, second, etc., may be used to describe various elements, but the elements are not limited by the terms. The above terms are used only for the purpose of distinguishing one component from another component. Therefore, a first component mentioned below may be a second component within the spirit of the present description.

A singular expression includes a plural expression unless the context clearly dictates otherwise. That is, a singular expression in the present disclosure and in the claims should generally be construed to mean "one or more" unless specified otherwise or if it is not clear from the context to refer to a singular form.

The terms such as "include" or "comprise" may be construed to denote a certain characteristic, number, step, operation, constituent element, or a combination thereof, but may not be construed to exclude the existence of or a possibility of addition of one or more other characteristics, numbers, steps, operations, constituent elements, or combinations thereof.

The term "or" in the present disclosure should be understood as "or" in an implicit sense and not "or" in an exclusive sense. That is, unless otherwise specified or clear from context, "X employs A or B" is intended to mean one of natural implicit substitutions. That is, when X employs A; when X employs B; or when X employs both A and B, "X employs A or B" can be applied to any one of these cases. Furthermore, the term "and/or" as used in the present disclosure should be understood to refer to and encompass all possible combinations of one or more of listed related items.

As used in the present disclosure, the terms "information" and "data" may be used interchangeably.

Unless otherwise defined, all terms (including technical and scientific terms) used in the present disclosure may be used with meanings that can be commonly understood by those of ordinary skill in the technical field of the present disclosure. Also, terms defined in general used dictionary are not to be excessively interpreted unless specifically defined.

However, the present disclosure is not limited to embodiments disclosed below and may be implemented in various different forms. Some embodiments of the present disclosure are provided merely to fully inform those of ordinary skill in the technical field of the present disclosure of the scope of the present disclosure, and the present disclosure is only defined by the scope of the claims. Therefore, the definition should be made based on the content throughout the present disclosure.

According to some embodiments of the present disclosure, at least one processor of a device (hereinafter referred to as a "processor") may identify a cognitive function state of a user based on first output data that is output after user information, at least one voice data, and speech time information related to the at least one voice data are input to a cognitive function state identification model.

Hereinafter, a system for identifying a cognitive function state of a user is described with reference to FIG. 1. A method of obtaining at least one voice data is described with reference to FIGS. 2 to 11. A method of identifying a cognitive function state of a user is described with reference to FIGS. 12 and 13.

FIG. 1 is a schematic diagram for explaining a system for identifying a user's cognitive function state according to some embodiments of the present disclosure.

Referring to FIG. 1, the system for identifying a user's cognitive function state may include a device 100 for identifying cognitive function state and a user terminal 200 for a user requiring identification of cognitive function status. In addition, communication between the device 100 and the user terminal 200 may be connected through the wired/wireless network 300. However, the components constituting the system shown in FIG. 1 are not essential for implementing a system for identifying the user's cognitive function state, and may have more or fewer components than the components listed above.

The device 100 of the present disclosure may be paired with or connected to the user terminal 200 over the wire/wireless network 300, thereby transmitting/receiving predetermined data. In this case, data transmitted/received over the wire/wireless network 300 may be converted before transmission/reception. In this case, the "wire/wireless network" 300 collectively refers to a communication network supporting various communication standards or protocols for pairing and/or data transmission/reception between the device 100 and the user terminal 200. The wire/wireless network 300 includes all communication networks to be supported now or in the future according to the standard and may support all of one or more communication protocols for the same.

The device 100 for identifying the user's cognitive function state may include a processor 110, storage 120, and a communication unit 130. The components illustrated in FIG. 1 are not essential for implementing the device 100, and thus, the device 100 described in the present disclosure may include more or fewer components than those listed above.

Each component of the device 100 of the present disclosure may be integrated, added, or omitted according to the specifications of the device 100 that is actually implemented. That is, as needed, two or more components may be combined into one component or one component may be subdivided into two or more components. In addition, a function performed in each block is for describing an embodiment of the present disclosure, and the specific operation or device does not limit the scope of the present disclosure.

The device 100 described in the present disclosure may include any device that transmits and receives at least one of data, content, service, and application, but the present disclosure is not limited thereto.

The device 100 of the present disclosure includes, for example, any standing devices such as a server, a personal computer (PC), a microprocessor, a mainframe computer, a digital processor and a device controller; and any mobile devices (or handheld device) such as a smart phone, a tablet PC, and a notebook, but the present disclosure is not limited thereto.

In an embodiment of the present disclosure, the term "server" refers to a device or system that supplies data to or receives data from various types of user terminals, i.e., a client.

For example, a web server or portal server that provides a web page or a web content (or a web service), an advertising server that provides advertising data, a content server that provides content, an SNS server that provides a social network service (SNS), a service server provided by a manufacturer, a multichannel video programming distributor (MVPD) that provides video on demand (VoD) or a streaming service, a service server that provides a pay service, or the like may be included as a server.

In an embodiment of the present disclosure, the device 100 means a server according to context, but may mean a fixed device or a mobile device, or may be used in an all-inclusive sense unless specified otherwise.

The processor 110 may generally control the overall operation of the device 100 in addition to an operation related to an application program. The processor 110 may provide or process appropriate information or functions by processing signals, data, or information that is input or output through the components of the device 100 or driving an application program stored in the storage 120.

The processor 110 may control at least some of the components of the device 100 to drive an application program stored in the storage 120. Furthermore, the processor 110 may operate by combining at least two or more of the components included in the device 100 to drive the application program.

The processor 110 may include one or more cores, and may be any of a variety of commercial processors. For example, the processor 110 may include a central processing unit (CPU), general purpose graphics processing unit (GPUGP), and tensor processing unit (TPU) of the device, but the present disclosure is not limited thereto.

The processor 110 of the present disclosure may be configured as a dual processor or other multiprocessor architecture, but the present disclosure is not limited thereto.

The processor 110 may identify the user's cognitive function status using the cognitive function status identification model according to some embodiments of the present disclosure by reading a computer program stored in the storage 120.

The storage 120 may store data supporting various functions of the device 100. The storage 120 may store a plurality of application programs (or applications) driven in the device 100, and data, commands, and at least one program command for the operation of the device 100. At least some of these application programs may be downloaded from an external server through wireless communication. In addition, at least some of these application programs may exist in the device 100 from the time of shipment for basic functions of the device 100. The application program may be stored in the storage 120, installed in the device 100, and driven by the processor 110 to perform the operation (or function) of the device 100.

The storage 120 may store any type of information generated or determined by the processor 110 and any type of information received through the communication unit 130.

The storage 120 may include at least one type of storage medium of a flash memory type, a hard disk type, a solid state disk (SSD) type, a silicon disk drive (SDD) type, a multimedia card micro type, a card-type memory (e.g., SD memory and XD memory), random access memory (RAM), static random access memory (SRAM), read-only memory (ROM), electrically erasable programmable read-only memory (EEPROM), programmable read-only memory (PROM), magnetic memory, a magnetic disk, and an optical disk. The device 100 may be operated in relation to a web storage that performs a storage function of the storage 120 on the Internet.

According to some embodiments of the present disclosure, the storage 120 may store a cognitive function state identification model for identifying a cognitive function state of a user. The processor 110 may identify a cognitive function state of a user by inputting user information, at least one voice data, and speech time information related to the at least one voice data to the cognitive function state identification model. This is described more specifically with reference to FIGS. 12 and 13.

In the present disclosure, the cognitive function state identification model may have a structure in which a plurality of models each having a neural network structure has been ensembled. In this case, the ensembled structure may mean a structure in which the output data of any one of the plurality of models is used as the input data of another of the plurality of models, but the present disclosure is not limited thereto.

The communication unit 130 may include one or more modules that enable wire/wireless communication between the device 100 and a wire/wireless communication system, between the device 100 and another device, or between the device 100 and an external server. In addition, the communication unit 130 may include one or more modules that connect the device 100 to one or more networks.

The communication unit 130 refers to a module for wired/wireless Internet connection, and may be built-in or external to the device 100. The communication unit 130 may be configured to transmit and receive wire/wireless signals.

The communication unit 130 may transmit/receive a radio signal with at least one of a base station, an external terminal, and a server on a mobile communication network constructed according to technical standards or communication methods for mobile communication (e.g., Global System for Mobile communication (GSM), Code Division Multi Access (CDMA), Code Division Multi Access 2000 (CDMA2000), Enhanced Voice-Data Optimized or Enhanced Voice-Data Only (EV-DO), Wideband CDMA (WCDMA), High Speed Downlink Packet Access (HSDPA), High Speed Uplink Packet Access (HSUPA), Long Term Evolution (LTE), Long Term Evolution-Advanced (LTE-A), etc.).

Examples of wireless Internet technology include Wireless LAN (WLAN), Wireless-Fidelity (Wi-Fi), Wireless Fidelity (Wi-Fi) Direct, Digital Living Network Alliance (DLNA), Wireless Broadband (WiBro), World Interoperability for Microwave Access (WiMAX), High Speed Downlink Packet Access (HSDPA), High Speed Uplink Packet Access (HSUPA), Long Term Evolution (LTE), and Long Term Evolution-Advanced (LTE-A). However, in a range including Internet technologies not listed above, the communication unit 130 may transmit/receive data according to at least one wireless Internet technology.

In addition, the communication unit 130 may be configured to transmit and receive signals through short range communication. The communication unit 130 may perform short range communication using at least one of Bluetooth™, Radio Frequency Identification (RFID), Infrared Data Association (IrDA), Ultra-Wideband (UWB), ZigBee, Near Field Communication (NFC), Wireless-Fidelity (Wi-Fi), Wi-Fi Direct and Wireless Universal Serial Bus (Wireless USB) technology. The communication unit 130 may support wireless communication through short range communication networks (wireless area networks). The short range communication networks may be wireless personal area networks.

The device 100 according to some embodiments of the present disclosure may be connected to the user terminal 200 and the wire/wireless network 300 through the communication unit 130.

In an embodiment of the present disclosure, the user terminal 200 may be paired with or connected to the device 100, in which the cognitive function state identification model is stored, over the wire/wireless network 300, thereby transmitting/receiving and displaying predetermined data.

The user terminal 200 described in the present disclosure may include any device that transmits, receives, and displays at least one of data, content, service, and application. In addition, the user terminal 200 may be a terminal of a user who wants to check cognitive function status, but the present disclosure is not limited thereto.

In an embodiment of the present disclosure, the user terminal 200 may include, for example, a mobile device such as a mobile phone, a smart phone, a tablet PC, or an ultrabook, but the present disclosure is not limited thereto. The user terminal 200 may include a standing device such as a Personal Computer (PC), a microprocessor, a mainframe computer, a digital processor, or a device controller.

The user terminal 200 includes a processor 210, storage 220, a communication unit 230, an image acquisition unit 240, a display unit 250, a sound output unit 260, and a sound acquisition unit 270. The components illustrated in FIG. 1 are not essential in implementing the user terminal 200, and thus, the user terminal 200 described in the present disclosure may have more or fewer components than those listed above.

Each component of the user terminal 200 of the present disclosure may be integrated, added, or omitted according to the specifications of the user terminal 200 that is actually implemented. That is, as needed, two or more components may be combined into one component, or one component may be subdivided into two or more components. In addition, the function performed in each block is for describing an embodiment of the present disclosure, and the specific operation or device does not limit the scope of the present disclosure.

The processor 210, storage 220, and communication unit 230 of the user terminal 200 are the same components as the processor 110, storage 120, and communication unit 130 of the device 100, and thus redundant descriptions thereof will be omitted, and differences between them are chiefly described below.

In the present disclosure, the processor 210 of the user terminal 200 may control the display unit 250 so that the display unit 250 displays a screen for obtaining at least one voice data.

For example, the processor 210 may obtain a plurality of first voice data of a user, while operating in conjunction with controlling the display unit 250 so that the display unit 250 sequentially displays a plurality of images related to one story. Furthermore, the processor 210 may obtain second voice data of the user, while operating in conjunction with controlling the display unit 250 so that the display unit 250 displays information on the one story without displaying an image. However, the present disclosure is not limited to such an example, and a detailed description thereof is described later with reference to FIGS. 2 to 7.

As another example, the processor 210 may control the display unit 250 so that the display unit 250 sequentially displays a first screen including a sentence so that a user can memorize the sentence and a second screen for obtaining the sentence that has been memorized by the user. Furthermore, the processor 210 may control the display unit 250 so that the display unit 250 displays a moving object in order to obtain information related to a change in the user's eyes before displaying the second screen. However, the present disclosure is not limited to such an example, and a detailed description thereof is described later with reference to FIGS. 8 to 11.

Meanwhile, since high processing speed and computational power are required to perform an operation using the cognitive function state identification model, the cognitive function state identification model may be stored only in the storage 120 of the device 100 and may not be stored in the storage 220 of the user terminal 200, but the present disclosure is not limited thereto.

The image acquisition unit 240 may include one or a plurality of cameras. That is, the user terminal 200 may be a device including one or plural cameras provided on at least one of a front part and rear part thereof.

The image acquisition unit 240 may process an image frame, such as a still image or a moving image, obtained by an image sensor. The processed image frame may be displayed on the display unit 250 or stored in the storage 220. The image acquisition unit 240 provided in the user terminal 200 may match a plurality of cameras to form a matrix structure. A plurality of image information having various angles or focuses may be input to the user terminal 200 through the cameras forming the matrix structure as described above.

The image acquisition unit 240 of the present disclosure may include a plurality of lenses arranged along at least one line. The plurality of lenses may be arranged in a matrix form. The plural lenses may be arranged in a matrix form. Such cameras may be called an array camera. When the image acquisition unit 240 is configured as an array camera, images may be captured in various ways using the plural lenses, and images of better quality may be obtained.

According to some embodiments of the present disclosure, the image acquisition unit 240 may obtain an image of the user terminal 200, including a user's eyes, while operating in conjunction with a moving object being displayed in the user terminal 200.

The display unit 250 may display (output) information processed by the user terminal 200. For example, the display unit 250 may display execution screen information of an application program driven in the user terminal 200, or user interface (UI) and graphic user interface (GUI) information according to the execution screen information.

The display unit 250 may include at least one of a liquid crystal display (LCD), a thin film transistor liquid crystal display (TFT LCD), an organic light-emitting diode (OLED), a flexible display, a 3D display, and an e-ink display, but the present disclosure is not limited thereto.

According to some embodiments, the display unit 250 may display a first screen including a sentence, a screen including a moving object, or a second screen in which the sentence is hidden under the control of the processor 210.

According to other some embodiments of the present disclosure, the display unit 250 may sequentially display a plurality of images related to one story and display information related to the one story without displaying an image, under the control of the processor 210.

The sound output unit 260 may output audio data (or sound data, etc.) received from the communication unit 230 or stored in the storage 220. The sound output unit 260 may also output a sound signal related to a function performed by the user terminal 200.

The sound output unit 260 may include a receiver, a speaker, or a buzzer. That is, the sound output unit 260 may be implemented as a receiver or may be implemented in the form of a loudspeaker, but the present disclosure is not limited thereto.

According to some embodiments of the present disclosure, the sound output unit 260 may output a preset sound (e.g., a voice that describes a work that needs to be performed by a user through at least one task) while operating in conjunction with performing the at least one task for obtaining at least one voice data, but the present disclosure is not limited thereto.

The sound acquisition unit 270 may process an external sound signal as electrical sound data. The processed sound data may be used in various ways according to a function (or a running application program) being performed by the user terminal 200. Various noise removal algorithms for removing noise generated in a process of receiving an external sound signal may be implemented in the sound acquisition unit 270.

In the present disclosure, the sound acquisition unit 270 may obtain at least one voice data obtained by recording a voice uttered by a user under the control of the processor 210. However, the present disclosure is not limited thereto.

According to some embodiments of the present disclosure, a digital biomarker (a biomarker obtained from a digital device) for identifying a cognitive function state may be obtained while a preset screen is displayed on a user terminal. Here, the digital biomarker may mean at least one voice data. This will be described below in detail with reference to FIGS. 2 to 11.

Figure 2:
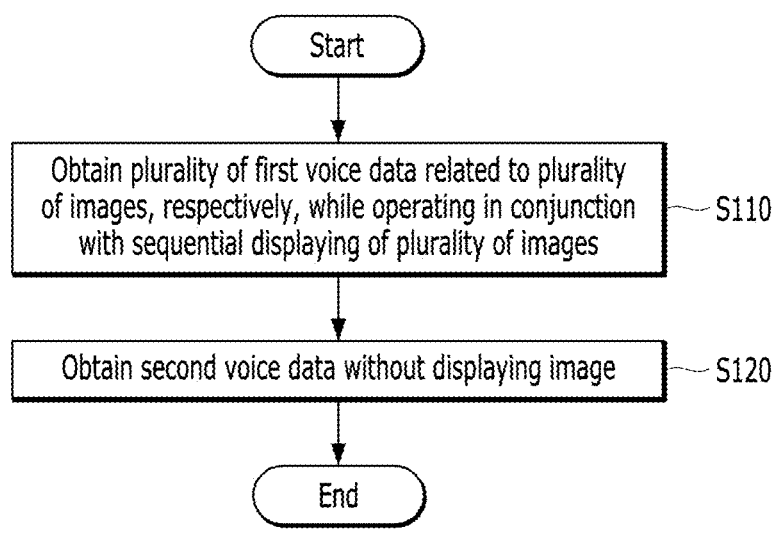
FIG. 2 is a flowchart for describing an example of a method of obtaining at least one voice data according to some embodiments of the present disclosure.
Figure 3:
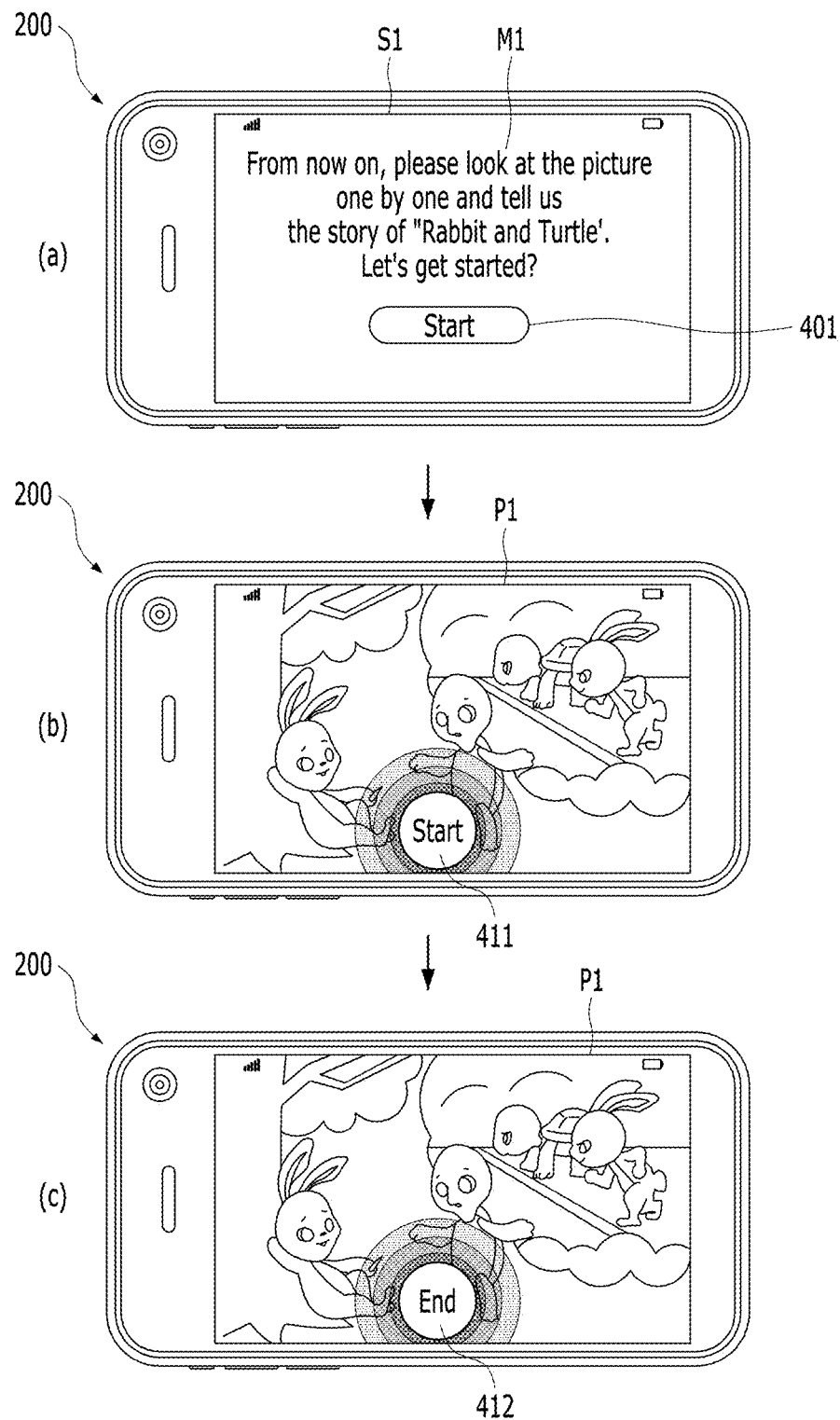
Figure 5:
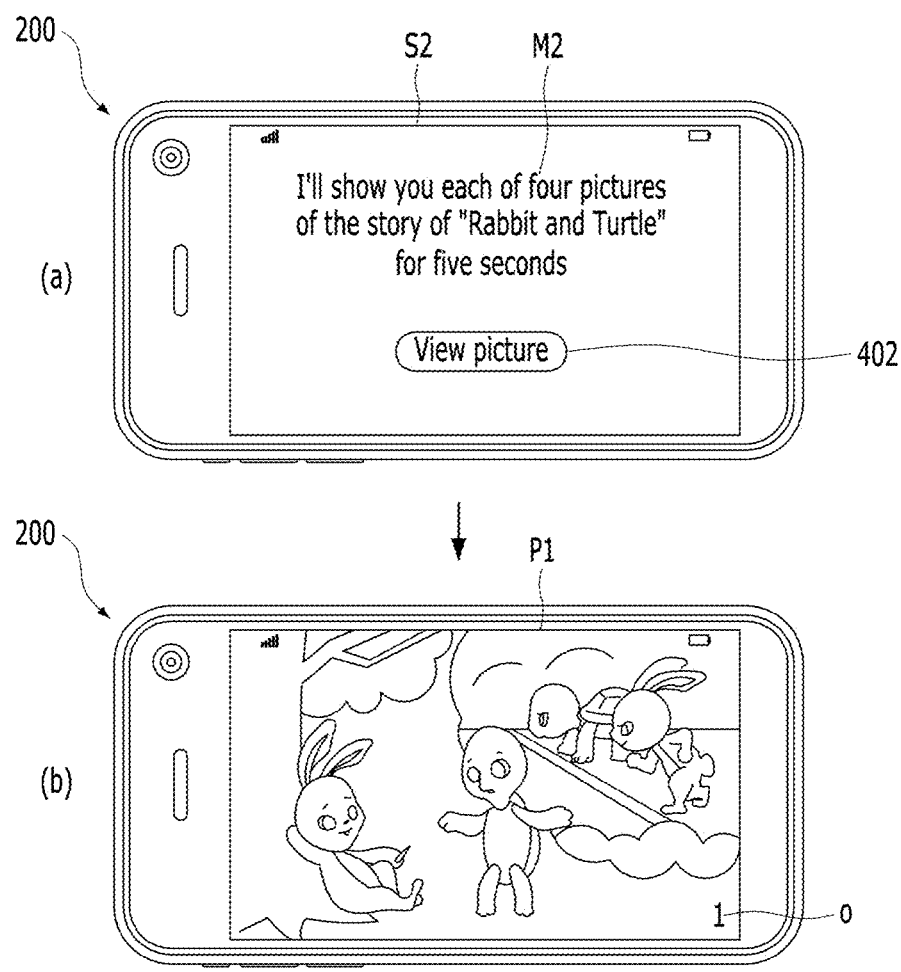
Figure 6:
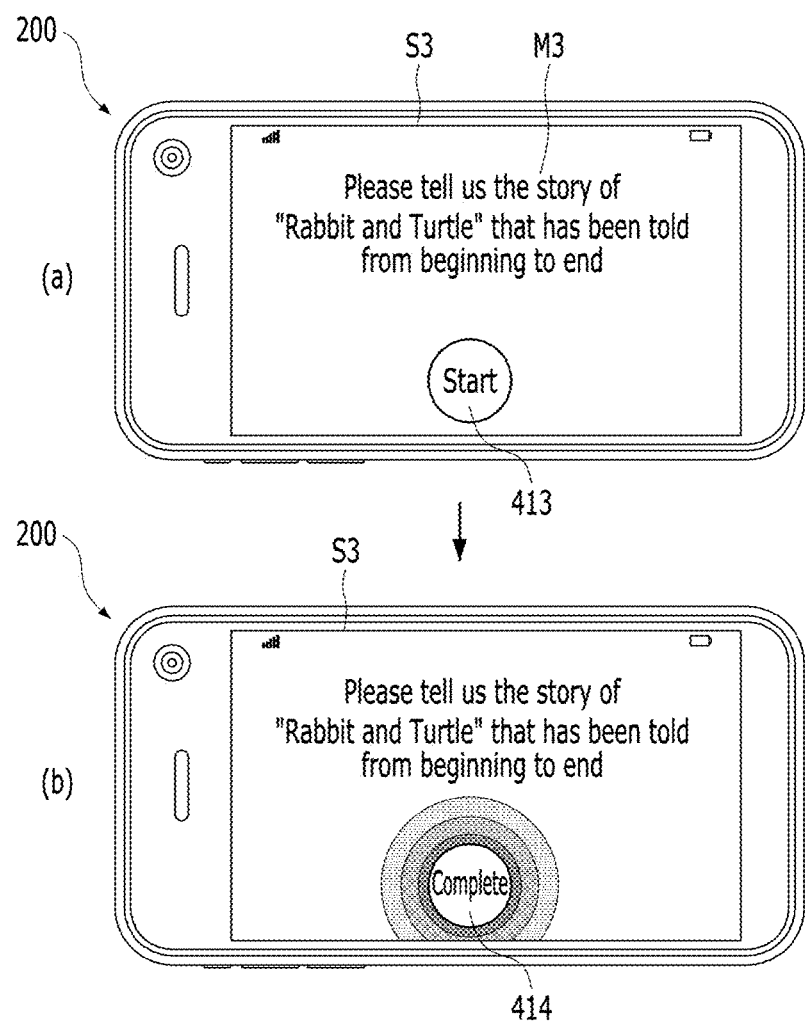
FIGS. 6 and 7 are diagrams for describing a plurality of images that are displayed when at least one voice data is obtained according to some embodiments of the present disclosure.
Figure 7:
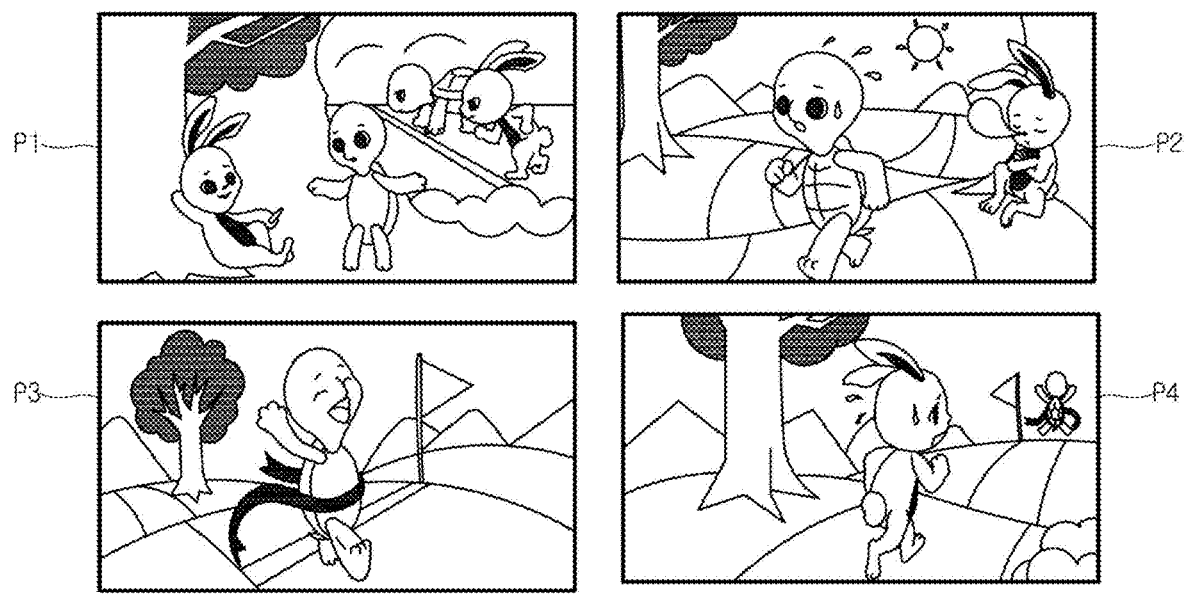

FIG. 2 is a flowchart for describing an example of a method of obtaining at least one voice data according to some embodiments of the present disclosure. FIGS. 3 to 5 are diagrams for describing an example of a method of obtaining at least one voice data according to some embodiments of the present disclosure. FIGS. 6 and 7 are diagrams for describing a plurality of images that are displayed when at least one voice data is obtained according to some embodiments of the present disclosure. In relation to FIGS. 2 to 7, contents that are redundant with the contents described in relation to FIG. 1 are not described, and a difference between them is chiefly described.

Referring to FIG. 2, the processor 110 of the device 100 may perform a first task for obtaining a plurality of first voice data related to a plurality of images, respectively, while operating in conjunction with causing the plurality of images to be sequentially displayed in the user terminal 200 (S110). In this case, the plurality of images is images related to one story, and may be sequentially displayed in the user terminal 200.

The plurality of first voice data may include voice data that is obtained from timing at which first touch input is input to the user terminal 200 to timing at which a second touch input is input, when an N-th (N is a natural number equal to or greater than 1) image, among a plurality of images, is displayed.

The first touch input may be a touch input to a button (e.g., the start button) that is displayed along with the N-th image.

The second touch input may be a touch input to a second button in the state in which the second button has been displayed along with the N-th image instead of the first button in response to the first touch input.

A process of obtaining the plurality of first voice data is more specifically described with reference to FIG. 3.

Referring to (a) in FIG. 3, before obtaining a plurality of first voice data, the processor 210 of the user terminal 200 may control the display unit 250 so that the display unit 250 displays a description screen S1 that describes a task that needs to be performed by a user. In this case, the description screen S1 may include a message M1 that describes the task that needs to be performed by the user and a start button 401 that enables the first task for obtaining the plurality of first voice data to be started.

According to some embodiments of the present disclosure, a sound related to the message M1 (e.g., a voice that describes contents included in the message M1) may be output through the sound output unit 260, while operating in conjunction with the displaying of the message M1. If a user is made cognitive of a task that needs to be performed by the user through the output of the sound along with the message M1 as described above, the user can clearly understand the task that is now being performed by the user. Accordingly, there may be a poor possibility that a user may perform an erroneous task due to simple mistakes.

Referring to (b) in FIG. 3, the processor 210 of the user terminal 200 may control the display unit 250 so that the display unit 250 displays a primary image P1, among a plurality of images, based on a touch input to select the start button 401.

Specifically, the processor 210 of the user terminal 200 may control the display unit 250 so that the display unit 250 also displays a first button 411, when the primary image P1, among the plurality of images, is displayed. In this case, the plurality of images is images related to one story, and may be images that are displayed in a display order. The primary image P1 may be the first image that is displayed for the first time.

Meanwhile, a method of displaying images if the plurality of images has been stored in the storage 120 of the device 100 and a method of displaying images if the plurality of images has been stored in the storage 220 of the user terminal 200 may be different from each other.

For example, if the plurality of images has been stored in the storage 120 of the device 100, the processor 210 of the user terminal 200 may control the communication unit 230 so that the communication unit 230 receives the primary image P1 after transmitting a primary image request signal to the device 100, when a touch input to select the start button 401 is detected. When receiving the primary image P1, the processor 210 of the user terminal 200 may control the display unit 250 so that the display unit 250 displays the primary image P1.

As another example, if the plurality of images has been stored in the storage 220 of the user terminal 200, the processor 210 may control the display unit 250 so that the display unit 250 displays the primary image P1, among the plurality of images that has been stored in the storage 220, when a touch input to select the start button 401 is detected.

Referring to (c) in FIG. 3, when a first touch input to the first button 411 is input, the processor 210 may start to obtain first voice data related to the primary image P1 by activating the sound acquisition unit 240, while operating in conjunction with the displaying of the second button 412 along with the primary image P1 instead of the first button.

When a touch input to the first button 411 is detected, a second button 412 may be displayed instead of the first button 411 while a preset effect is added to the second button 412. For example, an effect having a form in which a preset color is spread centering around the second button 412 may be added to the second button 412. However, the preset effect is not limited to the aforementioned example, and various effects may be added to the second button 412. When the preset effect is added to the second button 412 as described above, a user can cognize that the first voice data is now being obtained.

When a second touch input to the second button 412 is input, the processor 210 may terminate the acquisition of the first voice data and deactivate the sound acquisition unit 240. That is, the first voice data that is obtained when the primary image is displayed may be recorded voice data of a voice of a user from timing at which the first touch input is input to timing at which the second touch input is input. Furthermore, the first voice data that is obtained when the primary image is displayed may be recorded as the first voice data related to the primary image.

According to some embodiments of the present disclosure, when the second touch input to the second button 412 is input, the processor 210 may control the display unit 250 so that the display unit 250 displays a secondary image (P2 in FIG. 7) instead of the primary image P1. That is, an N-th image (N is a natural number equal to or greater than 1) may be changed into an (N+1)-th image in response to the second touch input.

Meanwhile, when the secondary image is displayed, the processor 210 may identically perform the aforementioned task in relation to (b) in FIG. 3 and (c) in FIG. 3. That is, when a touch input of a user for the second button 412 is detected as described above, the processor 210 may sequentially change an image into a next image, and may additionally obtain first voice data related to the next image. In this way, the processor 210 may obtain a plurality of first voice data related to all images that are related to a selected story.

According to some embodiments of the present disclosure, a plurality of images is images related to one story. The plurality of images may also be changed when a story title is different.

A plurality of images related to a plurality of stories, respectively, may be stored in the storage 120 of the device 100 or the storage 220 of the user terminal 200.

Referring to FIG. 6, a plurality of stories may have different story titles. In this case, the stories may be stories, such as Aesop's Fables and a children's story each having one plot.

For example, a plurality of stories may include at least a first story, a second story, a third story, and a fourth story. In this case, a story title of the first story may be Rabbit and Turtle, a story title of the second story may be Kongjwi Patjwi, a story title of the third story may be Sun and Moon, and a story title of the fourth story may be Heungbu and Nolbu, but the present disclosure is not limited thereto.

The number of images related to each of a plurality of stories may be the same or different.

For example, the number of images related to each of the first story, the second story, and the third story may be four. The number of images related to the fourth story may be five, but the present disclosure is not limited thereto.

In the present disclosure, a plurality of images that is displayed in the user terminal 200 may be images related to any one story, among the plurality of aforementioned stories.

Any one of the plurality of stories may be randomly selected, and may be selected in a preset order, but the present disclosure is not limited thereto.

Referring to FIG. 7, a plurality of images P1, P2, P3, and P4 related to one story may be different from each other, and may be stored in the storage 120 of the device 100 or the storage 220 of the user terminal 200, but the present disclosure is not limited thereto.

The order of each of the plurality of images P1, P2, P3, and P4 may have been determined. Accordingly, when the plurality of images P1, P2, P3, and P4 is displayed in the user terminal 200, the plurality of images P1, P2, P3, and P4 may be sequentially displayed.

Specifically, when a second touch input to the second button 412 that is displayed when the primary image P1 is displayed is detected, the secondary image P2 may be displayed on the display unit 250 of the user terminal 200. When a second touch input to the second button 412 that is displayed when the secondary image P2 is displayed is detected, the tertiary image P3 may be displayed on the display unit 250 of the user terminal 200. In this way, all of the plurality of images P1, P2, P3, and P4 may be displayed on the display unit 250 of the user terminal 200.

Meanwhile, according to some embodiments of the present disclosure, prior to the first task for obtaining the plurality of first voice data related to the plurality of images while operating in conjunction with the sequential displaying of the plurality of images, a task for sequentially displaying each of the plurality of images for a preset time may be performed without obtaining voice data. This is described in detail with reference to FIG. 4.

Referring to (a) in FIG. 4, prior to a task for sequentially displaying each of a plurality of images for a preset time, the processor 210 may control the display unit 250 so that the display unit 250 displays a description screen S2 that describes a task that needs to be performed by a user. In this case, the description screen S2 may include a message M2 that describes a task that needs to be performed by the user and a start button 402 that enables the task for sequentially displaying each of the plurality of images for a preset time to be started.

According to some embodiments of the present disclosure, a sound related to the message M2 (e.g., a voice that describes contents included in the message M2) may be output through the sound output unit 260, while operating in conjunction with the displaying of the message M2. If a user is made cognitive of a task that needs to be performed by the user through the output of the sound along with the message M2 as described above, the user can clearly understand the task that is now being performed by the user. Accordingly, the user's concentration can be improved.

Referring to (b) in FIG. 4, the processor 210 of the user terminal 200 may control the display unit 250 so that the display unit 250 first displays the primary image P1, among the plurality of images, based on a touch input to select the start button 402.

Specifically, the processor 210 of the user terminal 200 may control the display unit 250 so that the display unit 250 also displays information O related to the order of the primary image P1 when the primary image P1, among a plurality of images, is displayed. In this case, the plurality of images is images related to one story, and may be images that are displayed in their display orders. The primary image P1 may be the first image that is displayed for the first time.

The information O related to the order of an image may include a number. That is, since the primary image P1 is the first image, a number 1 may be included in the information O related to the order of the primary image P1, but the present disclosure is not limited thereto.

According to some embodiments of the present disclosure, the primary image may be changed into a secondary image after being displayed for a preset time (e.g., five seconds), but the present disclosure is not limited thereto.

When an image that is displayed on the display unit 250 of the user terminal 200 is changed into the secondary image, the information O related to the order of the image may also be changed.

For example, since the secondary image is the second image, a number 2 may be included in the information O related to the order of the secondary image, but the present disclosure is not limited thereto.

That is, an image that is displayed on the display unit 250 of the user terminal 200 may be sequentially changed. When the image is changed, the information O related to the order of the image may also be changed.

Referring back to FIG. 2, the processor 110 of the device 100 may perform a second task for obtaining second voice data without displaying an image in the user terminal (S120). Specifically, the processor 110 of the device 100 may perform the second task for obtaining the second voice data while operating in conjunction with causing information on one story to be displayed in the user terminal without displaying an image.

The second voice data may be voice data that is obtained from timing at which a third touch input is input to timing at which a fourth touch input is input on a screen that is displayed when a second task is performed, but the present disclosure is not limited thereto. In this case, the third touch input may be a touch input to a third button (e.g., the start button) that is displayed when the second task is performed.

Furthermore, the fourth touch input may be a touch input to a fourth button in the state in which the fourth button has been displayed instead of the third button, in response to the third touch input.

Specifically, referring to (a) in FIG. 5, before the second task is performed, the processor 210 may control the display unit 250 so that the display unit 250 displays a description screen S3 that describes a task that needs to be performed by a user. In this case, the description screen S3 may include a message M3 that describes a task that needs to be performed by a user and a start button 413 related to the acquisition of the second voice data. In this case, the message M3 may include contents indicating that a story related to a plurality of images displayed in the first task needs to be spoken.

According to some embodiments of the present disclosure, a sound related to the message M3 (e.g., a voice that describes contents included in the message M3) may be output through the sound output unit 260 while operating in conjunction with the displaying of the message M3. If a user is made cognitive of a task that needs to be performed by the user through the output of the sound along with the message M3 as described above, the user can clearly understand the task that is now being performed by the user. Accordingly, the user's concentration can be improved.

Referring to (b) in FIG. 5, when a touch input to select the third button 413 is input, the processor 210 of the user terminal 200 may control the display unit 250 so that the display unit 250 displays a fourth button 414 on the screen S3 instead of the third button 413. Furthermore, the processor 210 may start to obtain the second voice data by activating the sound acquisition unit 240 without displaying a separate image on the screen S3.

When a touch input to the third button 413 is detected, a preset effect may be displayed while the preset effect is added to the fourth button 414 that is displayed instead of the third button 413. For example, an effect having a form in which a preset color is spread around the fourth button 414 may be added to the fourth button 414. However, the preset effect is not limited to the aforementioned example, and various effects may be added to the fourth button 414. When the preset effect is added to the fourth button 414 as described above, a user can cognize that the second voice data is now being obtained.

When the fourth touch input to the fourth button 414 is input, the processor 210 may terminate the acquisition of the second voice data, and may deactivate the sound acquisition unit 240. That is, the second voice data may be recorded voice data of a voice of a user from timing at which the third touch input to select the third button 413 is input to timing at which the fourth touch input is input.

According to some embodiments of the present disclosure, the processor 210 of the user terminal 200 may control the communication unit 230 so that the communication unit 230 transmits the plurality of first voice data and the second voice data to the device 100.

For example, after obtaining all of the plurality of first voice data and the second voice data, the processor 210 may control the communication unit 230 so that the communication unit 230 transmits the plurality of first voice data and the second voice data to the device 100.

As another example, after obtaining all of the plurality of first voice data, the processor 210 may control the communication unit 230 so that the communication unit 230 transmits the plurality of first voice data to the device 100. Furthermore, after obtaining the second voice data, the processor 210 may control the communication unit 230 so that the communication unit 230 transmits the second voice data to the device 100. That is, before the second task is performed after all of the plurality of first voice data is obtained through the first task, the processor 210 may control the communication unit 230 so that the communication unit 230 first transmits the plurality of first voice data to the device 100 and then transmits the second voice data to the device 100.

As still another example, the processor 210 may control the communication unit 230 so that the communication unit 230 transmits the plurality of first voice data and the second voice data to the device 100 whenever the plurality of first voice data and the second voice data are obtained.

However, the aforementioned examples are merely examples of the present disclosure, and the present disclosure is not limited to the aforementioned examples.

Figure 8:
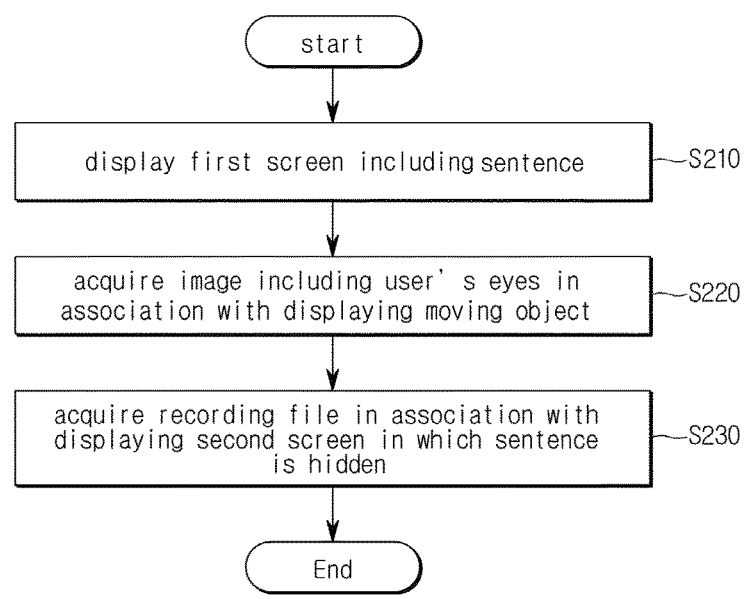
FIG. 8 is a flowchart for describing another example of a method of obtaining at least one voice data according to some embodiments of the present disclosure.
Figure 9:
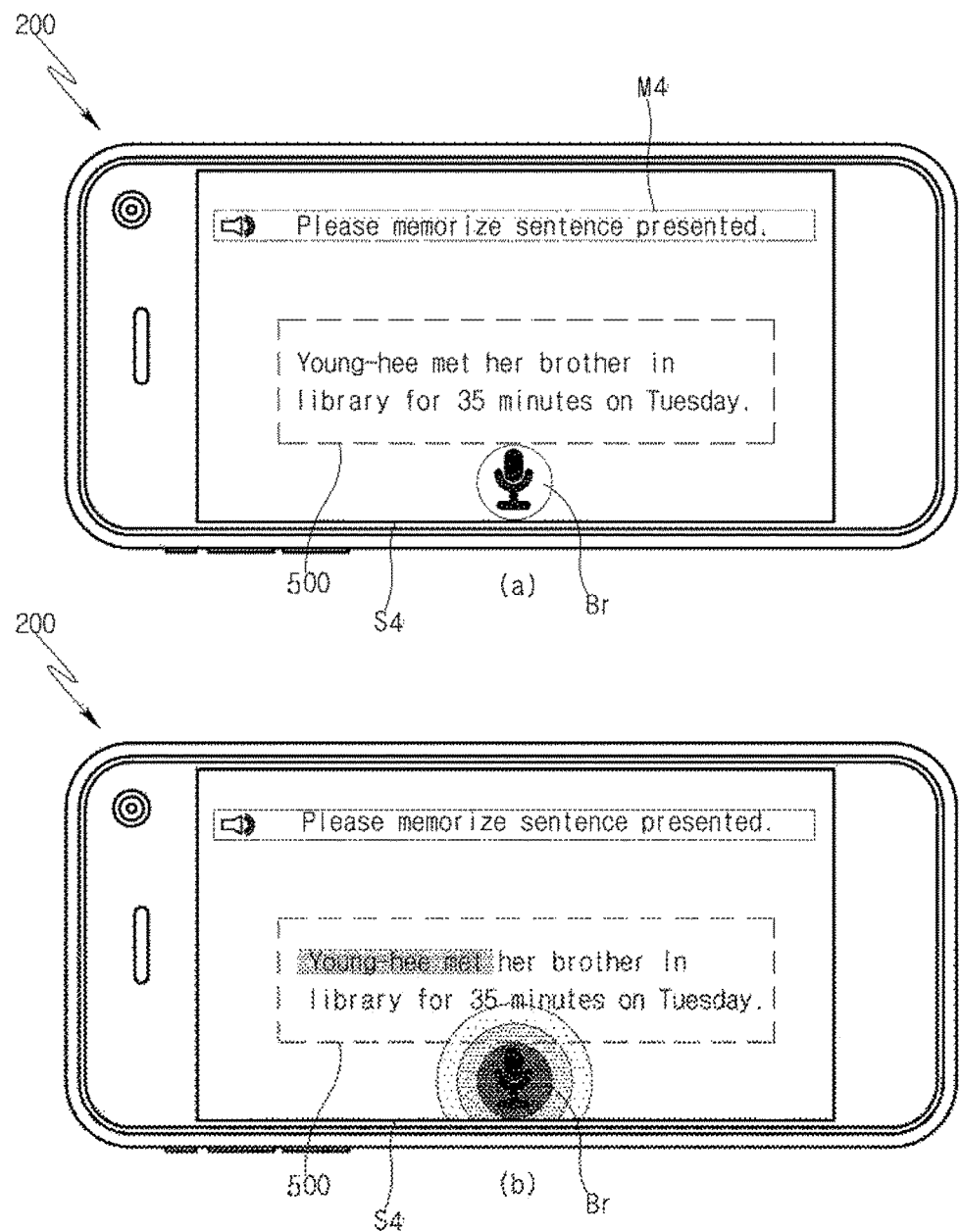
FIGS. 9 to 11 are diagrams for describing another example of a method of obtaining at least one voice data according to some embodiments of the present disclosure.
Figure 10:
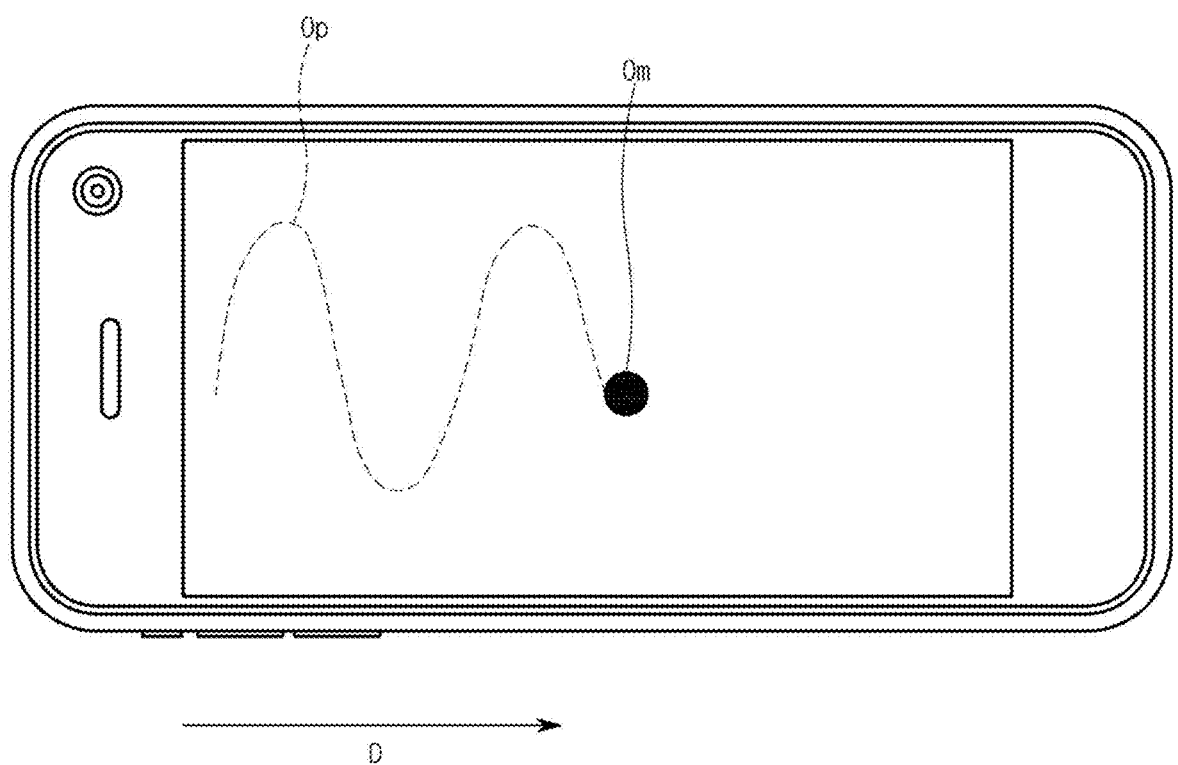
Figure 11:
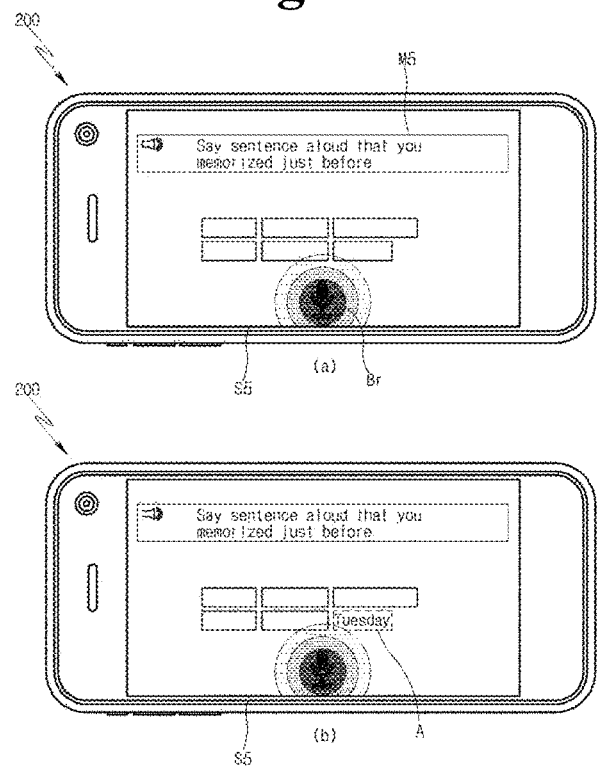

FIG. 8 is a flowchart for describing another example of a method of obtaining at least one voice data according to some embodiments of the present disclosure. FIGS. 9 to 11 are diagrams for describing another example of a method of obtaining at least one voice data according to some embodiments of the present disclosure. In relation to FIGS. 8 to 11, contents that are redundant with the contents described in relation to FIGS. 1 to 7 are not described again, and a difference between them is chiefly described.

Referring to FIG. 8, the processor 110 of the device 100 may perform the third task of causing the first screen including a sentence to be displayed on the user terminal 200 (S210).

For example, a plurality of sentences may be stored in the storage 120 of the device 100. Here, the plural sentences may be sentences generated according to the six-fold principle by using different words. In addition, the lengths of the plural sentences may be different from each other. The processor 110 may control the communication unit 130 to select one sentence among the plural sentences stored in the storage 120 and to transmit a signal for displaying the sentence to the user terminal 200. When the signal is received through the communication unit 230, the processor 210 of the user terminal 200 may control the display unit 250 to display the sentence included in the signal.

As another example, a plurality of words may be stored in the storage 120 of the device 100. Here, the plural words may be words having different word classes and different meanings. The processor 110 of the device 100 may combine at least some of a plurality of words based on a preset algorithm to generate a sentence conforming to the six-fold principle. The processor 110 may control the communication unit 130 to transmit a signal to display a generated sentence to the user terminal 200. When the signal is received through the communication unit 230, the processor 210 of the user terminal 200 may control the display unit 250 to display a sentence included in the signal.

As another example, a plurality of sentences may be stored in the storage 220 of the user terminal 200. Here, the plural sentences may be sentences generated according to the six-fold principle using different words. In addition, the lengths of the plural sentences may be different from each other. The processor 110 of the device 100 may transmit a signal to display a screen including a sentence to the user terminal 200. In this case, the processor 210 of the user terminal 200 may control the display unit 250 to select and display any one sentence among the plural sentences stored in the storage 220.

As another example, a plurality of words may be stored in the storage 220 of the user terminal 200. Here, the plural words may be words having different word classes and different meanings. The processor 110 of the device 100 may transmit a signal to display a screen including a sentence to the user terminal 200. In this case, the processor 210 of the user terminal 200 may combine at least some of the plurality words stored in the storage 220 based on a preset algorithm to generate a sentence conforming to the six-fold principle. In addition, the processor 210 may control the display unit 250 to display the generated sentence.

The aforementioned embodiments are merely examples for description of the present disclosure, and the present disclosure is not limited to the aforementioned embodiments.

Step S210 in the present disclosure will be described in more detail with reference to FIG. 9.

Referring to FIG. 9(a), the processor 110 of the device 100 may perform a third task of causing a first screen S1 including a sentence 400 to be displayed on the user terminal 200. Here, the sentence 400 may be a sentence generated according to the six-fold principle using different words.

In the present disclosure, the first screen S4 may include a recording button Br. Here, the recording button Br may be displayed on the first screen S4 in a state in which a touch input to the recording button is deactivated for a preset time. That is, the third task may include a first sub-task causing the user terminal 200 to display the first screen S4 for a preset time in a state in which a touch input to the recording button Br is inactivated.

When the preset time has elapsed, the processor 210 of the user terminal 200 may activate a touch input for the recording button Br. That is, the third task may include a second sub-task for activating a touch input to the recording button Br included in the first screen S4 when the preset time has elapsed.

For example, the processor 110 of the device 100 may check whether a preset time has elapsed from the time the first screen S4 is displayed. When the processor 110 recognizes that the preset time has elapsed from the time when the first screen S4 is displayed, the processor 110 may transmit a signal to activate the recording button Br to the user terminal 200. When receiving the signal, the user terminal 200 may activate a touch input for the recording button Br.

As another embodiment, the processor 210 of the user terminal 200 may check whether the preset time has elapsed from the time the first screen S4 is displayed. When the processor 210 recognizes that the preset time has elapsed from the time when the first screen S4 is displayed, the processor 210 may activate a touch input for the recording button Br.

However, the aforementioned embodiments are provided to describe examples of the present disclosure, and the present disclosure is not limited to the aforementioned embodiments.

Meanwhile, according to some embodiments of the present disclosure, the color of at least one word constituting the sentence included in the first screen S4 may be sequentially changed regardless of activation of a touch input for the recording button Br.

For example, when a preset time has elapsed (e.g., 1 to 2 seconds) after the first screen S4 is displayed on the user terminal 200, the color of at least one word constituting the sentence included in the first screen S4 may be changed in order. In this case, the touch input to the recording button Br may be activated or deactivated.

More specifically, the processor 110 may check whether a preset time has elapsed after the first screen S4 is displayed on the user terminal 200. In addition, when it is recognized that the preset time has elapsed, the processor 110 may control the communication unit 130 to transmit a signal to change at least one color constituting the sentence included in the first screen S4 to the user terminal 200. In this case, the processor 210 of the user terminal 200 may control the display unit 250 to sequentially change the color of at least one word constituting the sentence included in the first screen S4 as the signal is received. However, a method of sequentially changing the color of at least one word constituting the sentence included in the first screen S4 is not limited to the aforementioned embodiment.

As another example, the processor 110 may cause the color of at least one word constituting the sentence included in the first screen S4 to be sequentially changed immediately after the first screen S4 is displayed on the user terminal 200. In this case, the signal to display the first screen S4 may include a signal to sequentially change at least one color constituting the sentences included in the first screen S4, and, when the user terminal 200 displays the first screen S1, the color of at least one word constituting the sentences included in the first screen S4 may be sequentially changed. In this case, a touch input to the recording button Br may be activated or deactivated.

As still another example, the touch input of the recording button Br included in the first screen S4 may maintain an activated state from the beginning. When the processor 110 recognizes that a touch input is detected on the recording button Br after the first screen S4 is displayed on the user terminal 200, at least It may cause the color of one word to change in sequence, the color of at least one word constituting the sentence included in the first screen S4 may be sequentially changed.

More specifically, when a touch input to the recording button Br included in the first screen S4 is detected, the processor 210 of the user terminal 200 may control the communication unit 230 to transmit information indicating that a touch on the recording button Br has been performed to the device 100. When the processor 110 of the device 100 receives the information from the user terminal 200 through the communication unit 130, the processor 110 may recognize that a touch input to the recording button Br is detected. In addition, the processor 110 may control the communication unit 130 to transmit a signal to change at least one color constituting the sentence included in the first screen S4 to the user terminal 200. In this case, the processor 210 of the user terminal 200 may control the display unit 250 to sequentially change the color of at least one word constituting the sentence included in the first screen S4 as the signal is received. However, a method of sequentially changing the color of at least one word constituting the sentence included in the first screen S4 is not limited to the above-described embodiment.

Meanwhile, according to some embodiments of the present disclosure, the first screen S4 may include a message M4 informing a user of a task to be performed through a currently displayed screen. For example, the message M4 may include content to memorize a sentence included in the first screen S4. However, the present disclosure is not limited thereto.

According to some embodiments of the present disclosure, a sound (e.g., a voice explaining the content included in the message M4) related to the message M4 through the sound output unit 260 may be output in association with display of the message M4. In this way, when outputting a sound together with the message M4 to let the user know what the user needs to do, it is possible to clearly understand what the user is currently doing. Therefore, the possibility of performing a wrong operation by a simple mistake may be reduced.

Meanwhile, referring to FIG. 9(b), when a touch input to the recording button Br is detected after the recording button Br is activated, the processor 210 of the user terminal 200 may control the display unit 250 so that the color of at least one word constituting the sentence 400 included in the first screen S4 is sequentially changed. Here, when the color of at least one word is sequentially changed, only the color of a text may be changed, or the color may be changed in a form in which the text is highlighted with color in as shown in FIG. 9(b). That is, the third task may include a third sub-task that causes the color of at least one word included in the sentence 400 included in the first screen S4 to be sequentially changed according to a touch input to the recording button included in the first screen S4.

For example, the processor 210 of the user terminal 200 may control the communication unit 230 to generate a specific signal according to a touch input to the recording button Br and transmit the signal to the device 100. When receiving the specific signal through the communication unit 130, the processor 110 of the device 100 may transmit a signal to sequentially change the color of at least one word constituting the sentence 400 included in the first screen S4 to the user terminal 200. When receiving the signal through the communication unit 230, the processor 210 of the user terminal 200 may control the display unit 250 to sequentially change the color of at least one word constituting the sentence 400 included in the first screen S4.

As another example, the processor 210 of the user terminal 200 may control the communication unit 230 to transmit a signal indicating that the recording button Br is selected to the device 100 according to a touch input to the recording button Br. Next, the processor 210 of the user terminal 200 may control the display unit 250 to sequentially change the color of at least one word constituting the sentence 400 included in the first screen S4. That is, the user terminal 200 may control the display unit 250 such that the color of at least one word constituting the sentence 400 included in the first screen S4 is sequentially changed immediately without receiving a separate signal from the device 100.

Meanwhile, from the first word among at least one word constituting the sentence 400 included in the first screen S1, the color thereof may be sequentially changed.

For example, if the sentence 400 included in the first screen S4 is "Young-hee met her brother in the library for 35 minutes on Tuesday", the processor 210 may control the display unit 250 such that the color of the first word ("Young-hee") of the sentence 400 is first changed. In addition, the processor 210 may control the display unit 250 to change the second word to the same color as the first word after a preset time (e.g., 1 to 2 seconds) has elapsed. In this way, the processor 210 may sequentially change the colors of all of at least one word constituting the sentence 400 included in the first screen S4.

The processor 210 of the present disclosure may control the display unit 250 to sequentially change the color of at least one word of the sentence 400 upon receiving a specific signal by itself or from the device 100.

When the sentence 400 is simply displayed on the first screen S4, the user may not read the entire sentence. However, when the color of at least one word constituting the sentence 400 is sequentially changed as the user touches the recording button Br as described above, the user is more likely to read the sentence as a whole. That is, the problem that the second test is not properly performed because a user does not read the sentence 400 as a whole may be solved through the above-described embodiment.

Meanwhile, according to some embodiments of the present disclosure, when a touch input to the recording button Br is detected, a preset effect may be added to the recording button Br and displayed. For example, an effect having a form wherein a preset color spreads around the recording button Br may be added to the recording button Br. However, a preset effect is not limited to the above-described embodiment, and various effects may be added to the recording button Br. In the case that a touch input to the recording button Br is detected as described, a user may recognize that recording is currently in progress when a preset effect is added to the recording button Br.

Meanwhile, referring back to FIG. 8, the processor 110 may perform the fourth task of causing the user terminal 200 to acquire an image including the user's eyes in conjunction with displaying a moving object instead of the first screen (S120).

In the present disclosure, the moving object may be an object that moves along a preset path in a specific direction at a preset speed.

The preset path may be a path moving to have a cosine wave or a sine wave. However, the present disclosure is not limited thereto, and the preset path may be a path that moves to have various shapes (e.g., a clock shape, etc.).

When a moving speed of the moving object is 20 deg/sec to 40 deg/sec, it is possible to accurately identify the user's cognitive function status while stimulating the user's gaze. Accordingly, the preset speed may be 20 deg/sec to 40 deg/sec. However, the present disclosure is not limited thereto.

The specific direction may be a direction from left of the screen to right thereof or a direction from right of the screen to left thereof. However, the present disclosure is not limited thereto.

In the present disclosure, the moving object may be an object having a specific shape of a preset size. For example, the object may be a circular object with a diameter of 0.2 cm. When the object having the above-described shape moves, the user's gaze may move smoothly along the object.

Step S220 will be described in more detail with reference to FIG. 10.

Referring to FIG. 10, a moving object Om displayed on the user terminal 200 may move in a specific direction D along a preset path Op at a preset speed.

In the present disclosure, the moving object Om may be an object having a specific shape of a preset size. For example, the moving object Om may be a circular object having a diameter of 0.2 cm. When the object Om having the shape of the aforementioned size moves, the user's gaze may move smoothly along the object.

In the present disclosure, the preset path Op may be a path that moves to have a cosine waveform or a sine waveform. an amplitude of the cosine waveform or an amplitude of the sine waveform may be constant. However, the present disclosure is not limited thereto.

When the preset speed is 20 deg/sec to 40 deg/sec, it may be appropriate to accurately identify the user's cognitive function status while stimulating the user's gaze. Accordingly, the preset speed may be 20 deg/sec to 40 deg/sec. However, the present disclosure is not limited thereto.

The specific direction D may be a direction from left to right of the screen or a direction from right to left of the screen. However, the present disclosure is not limited thereto.

According to some embodiments of the present disclosure, a screen informing the user of a task to be performed may be displayed before performing the fourth task after performing the third task. That is, when the third task is completed, a screen including a message informing the user of the task to be performed in the fourth task may be displayed on the user terminal 200.

Meanwhile, although not shown in FIG. 10, the screen on which the moving object is displayed may include a message informing the user of the task to be performed through the currently displayed screen. For example, the message may include a message to gaze at the moving object. However, the present disclosure is not limited thereto.

According to some embodiments of the present disclosure, a sound (e.g., a voice explaining content included in the message) related to the message may be output through the sound output unit 260 in association with display of the message. In this way, when a sound is output together with the message to make the user aware of a task to be performed by the user, the user may clearly understand what the user currently needs to do. Therefore, the possibility of performing a wrong operation by a simple mistake may be reduced.

Meanwhile, referring back to FIG. 8, the processor 110 may perform the fifth task of causing the user terminal to acquire the recording file in conjunction with displaying the second screen in which sentences are hidden (S230). Here, the sentences hidden in the second screen may be the same as the sentences included in the first screen in step S210. Accordingly, after the user memorizes the sentences displayed on the first screen, the user may proceed with the second test in a manner of speaking the sentences when the second screen is displayed.

Step S230 in the present disclosure will be described in more detail with reference to FIG. 11.

Referring to FIG. 11(*a*), the processor 210 of the user terminal 200 may display the second screen S5 in which a sentence is hidden. Here, the second screen S5 may be a screen in which at least one word constituting the sentence is separated and hidden such that it can be known how many words the sentence is composed of. As described above, when at least one word is separated and hidden, the user may check the number of words. Therefore, the user may naturally come up with the previously memorized sentence by checking the number of words.

In the present disclosure, the second screen S5 may include the recording button Br as in the first screen S4. However, unlike when the first screen is displayed, the recording button Br may be in a state in which the touch input is continuously activated.

In some embodiments of the present disclosure, when a touch input that the user touches the recording button Br is detected, the processor 110 of the device 100 may cause the user terminal 200 to acquire the recording file.

Specifically, when a touch input for touching the recording button Br is detected, the processor 210 of the user terminal 200 may acquire the recording file including the user's voice through the sound acquisition unit 270. The processor 210 may control the communication unit 230 to transmit the recording file to the device 100. In this case, the processor 110 of the device 100 may acquire the recording file by receiving the recording file through the communication unit 130.

Meanwhile, when a touch input to the recording button Br is detected, a preset effect may be added to the recording button Br and displayed. For example, an effect in the form of spreading a preset color around the recording button Br may be added to the recording button Br. However, the preset effect is not limited to the above-described embodiment, and various effects may be added to the recording button Br. As described above, when a touch input to the recording button Br is detected and a preset effect is added to the recording button Br, the user may recognize that recording is currently in progress.

According to some embodiments of the present disclosure, the second screen S5 may include a message M5 informing the user of a task to be performed through the currently displayed screen. For example, the message M5 may include the content "say aloud the memorized sentence.". However, the present disclosure is not limited thereto.

According to some embodiments of the present disclosure, a sound (e.g., a voice explaining the content included in the message M5) related to the message M5 may be output through the sound output unit 260 in association with display of the message M5. In this way, when a sound is output together with the message M5 to allow the user to recognize a task to be performed by the user, it is possible to clearly understand what task the user should currently perform. Therefore, the possibility of performing a wrong operation due to a simple mistake may be reduced.

Meanwhile, referring to FIG. 11(*b*), the second screen may be displayed in a form in which a specific word A among at least one word constituting a sentence is displayed and other words except for the specific word A are hidden. Here, the specific word A may be a word including a predicate or a word disposed at the end of a sentence. However, the present disclosure is not limited thereto.

As described above, when the specific word A is not hidden and is displayed on the second screen, the specific word A may be a hint for memorizing the 'entire sentence memorized by the user.

When the user has a cognitive impairment, the user cannot memorize the entire sentence even if the specific word A is displayed. However, when the user does not have a cognitive impairment, the user may memorize the entire sentence when the specific word A is displayed. Therefore, when the specific word A is displayed without being hidden by the second screen, and then the acquired recording file is analyzed and utilized as a digital biomarker for analyzing cognitive function status, the accuracy of cognitive function status identification may be increased.

According to some embodiments of the present disclosure, the processor 110 of the device 100 may analyze the user's gaze change and voice data to identify the user's cognitive function state.

Meanwhile, according to some embodiments of the present disclosure, the third task causing the user terminal to display a first screen including a sentence; the fourth task causing the user terminal to acquire an image including the user's eyes in conjunction with displaying a moving object instead of the first screen; and the fifth task causing the user terminal to acquire a recording file in conjunction with displaying a second screen in which the sentences are hidden may be performed by a preset round. Here, at least one of the speed of the moving object and the direction in which the moving object moves may be changed as the round is changed. In addition, the sentences related to the third task and the fifth task may be changed as the round is changed.

For example, the speed of the moving object when performing the fourth task in a first round may be slower than the speed of the moving object when performing the fourth task in a next round. In addition, if the moving object moves from left to right when the fourth task is performed in the first round, the moving object may move from left to right when the fourth task is performed in the next round. In addition, the sentence when performing the third task and the fifth task in the first round may be a sentence having a first length, and the sentence when performing the third task and the fifth task in the next round is longer than the first length may be a sentence having a second length that is longer than the first length. However, the present disclosure is not limited thereto.

According to some embodiments of the present disclosure, when obtaining at least one voice data, the processor 110 of the device 100 may identify a cognitive function state of a user, based on at least one voice data, speech time information related to the at least one voice data, and user information. This is described more specifically with reference to FIGS. 12 and 13.

Figure 12:
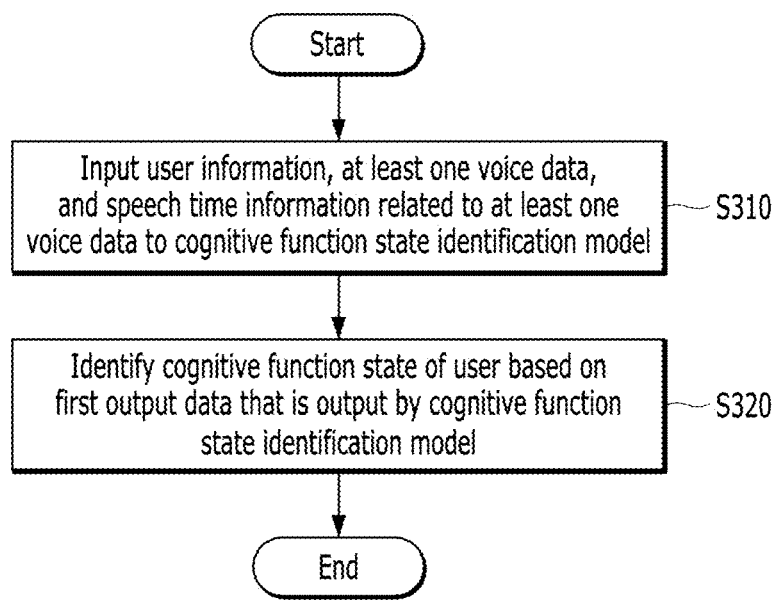
FIG. 12 is a flowchart for describing an example of a method of identifying a cognitive function state of a user according to some embodiments of the present disclosure.
Figure 13:
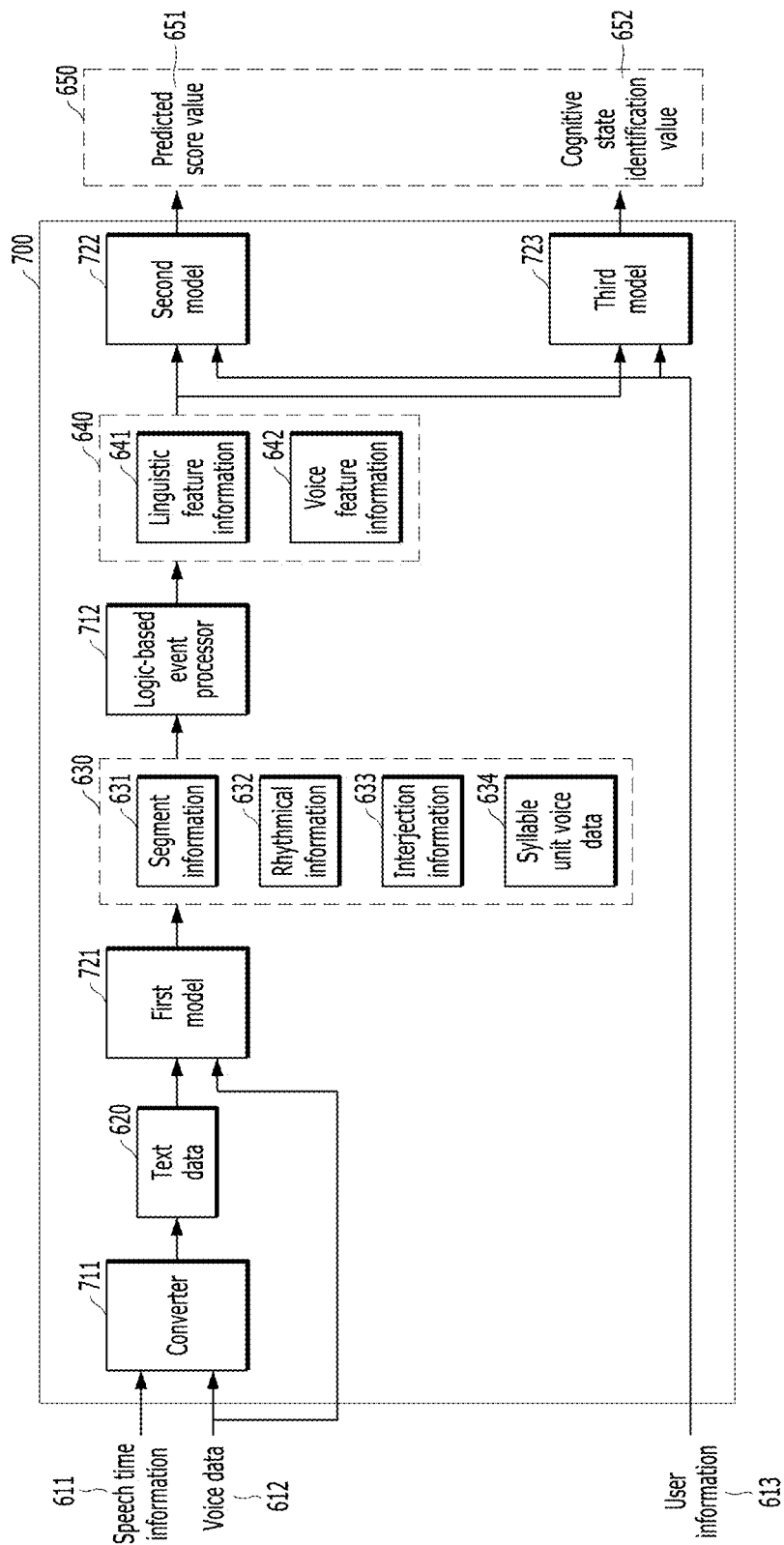
FIG. 13 is a diagram for describing an example of a method of identifying a cognitive function state of a user according to some embodiments of the present disclosure.

FIG. 12 is a flowchart for describing an example of a method of identifying a cognitive function state of a user according to some embodiments of the present disclosure. FIG. 13 is a diagram for describing an example of a method of identifying a cognitive function state of a user according to some embodiments of the present disclosure. In relation to FIGS. 12 and 13, contents that are redundant with the contents described in relation to FIGS. 1 to 11 are not described again, and a difference between them is chiefly described. Referring to FIG. 12, the processor 110 of the device 100 may input user information, at least one voice data, and speech time information related to the at least one voice data to the cognitive function state identification model (S310).

In the present disclosure, the at least one voice data may be obtained by using at least one of a method of obtaining first voice data and a method of obtaining second voice data, which is different from the method of obtaining the first voice data.

The method of obtaining the first voice data may include a step of performing a first task for obtaining a plurality of first voice data related to a plurality of images related to one story, respectively, while operating in conjunction with causing the plurality of images to be sequentially displayed in the user terminal 200 one by one and a step of performing a second task for obtaining the second voice data while operating in conjunction with causing information on the one story to be displayed in the user terminal 200 without displaying an image. Such contents are redundant with the contents described with reference to FIGS. 2 to 7, and a detailed description of the contents is obtained.

The method of obtaining the second voice data may include a step of performing a third task for causing the user terminal 200 to display a first screen including a sentence, a step of performing a fourth task for causing the user terminal 200 to obtain an image including a user's eyes while operating in conjunction with displaying a moving object instead of the first screen, and a step of performing a fifth task for causing the user terminal 200 to obtain a recording file including at least one voice data while operating in conjunction with displaying a second screen on which the sentence has been hidden. Such contents are redundant with the contents described with reference to FIGS. 8 to 11, and a detailed description thereof is omitted.

In the present disclosure, the user information may include at least one of information on the age and sex of a user and cognitive test result data of the user.

The user may directly input the information on his or her age and sex to his or her user terminal 200 in order to identify his or her cognitive function state. The information on the age and sex may be used when the cognitive function state of the user is identified. That is, the information on the age and sex of the user is information that has been input to the user terminal 200 by the user. The processor 110 of the device 100 may obtain the corresponding information through the communication unit 130, but the present disclosure is not limited thereto. The information on the age and sex of the user included in the user information may also be obtained through an external server.

The cognitive test result data of the user may mean data that is obtained after the user performs a cognitive test such as a memory test or a stroop test. The cognitive test result data may be obtained through the user terminal 200 or may be received through a server after a separate external test is performed, but the present disclosure is not limited thereto.

In the present disclosure, the user information may be managed in the form of global medical records (GMRs), and may be pre-processed in a form in which the user information can be immediately input to the cognitive function state identification model and stored in the storage 120, but the present disclosure is not limited thereto.

In the present disclosure, the speech time information may be information indicative of the length of a speech time of a voice that is included in each of one or more voice data. For example, information, such as one minute, may be included in speech time information related to voice data that is obtained by recording the talking of a user for one minute, but the present disclosure is not limited thereto.

After the user information, the at least one voice data, and the speech time information related to the at least one voice data are input to the cognitive function state identification model in step S310, the processor 110 may identify a cognitive function state of the user based on first output data that is output by the cognitive function state identification model (S320).

Referring to FIG. 13, when speech time information 611 related to at least one voice data, the at least one voice data 612, and user information 613 are input to the cognitive function state identification model 700, first output data 650 may be output.

The first output data 650 may include at least one of a predicted score value 651 and a cognitive state identification value 652, but the present disclosure is not limited thereto.

The cognitive function state identification model 700 may include at least one of a converter 711, a logic-based event processor 712, a first model 721, a second model 722, and a third model 723, but the present disclosure is not limited thereto. The cognitive function state identification model 700 may include components that are more or less than the aforementioned components.

The cognitive function state identification model 700 may have a structure in which a plurality of models has been ensembled. In this case, the ensembled structure may mean a structure in which the output data of any one of the plurality of models is used as the input data of another of the plurality of models. That is, the ensemble structure is a structure in which stacked models are sequentially used, and may mean a model into which both data characteristics and results can be simultaneously incorporated, but the present disclosure is not limited thereto.

Specifically, when the speech time information 611 and the at least one voice data 612 are input to the converter 711, the converter 711 may output text data 620. The text data 620 that is output by the converter 711 may be input to the first model 721. Second output data 630 that is output by the first model 721 may be input to the logic-based event processor 712. Furthermore, data 640 that is output by the logic-based event processor 712 and the user information 613 may be input to at least one of the second model 722 and the third model 723. In this case, the data 640 that is output by the logic-based event processor 712 may be ensemble with the user information 613 in a data perturbation way, and may be input to the second model 722 and the third model 723.

In the present disclosure, the converter 711 may convert the at least one voice data 612 into the text data 620, based on the at least one voice data 612 and the speech time information 611 related to the at least one voice data.

The converter 711 may convert the at least one voice data into the text data by using an algorithm related to a voice recognition technology (e.g., speech to text (STT)). For example, the algorithm related to the voice recognition technology may include a hidden Markov model (HMM), but the present disclosure is not limited thereto.

The first model 721 may generate the second output data 630 based on the text data 620. In this case, the second output data 630 may include word segment information 631, rhythmical information 632, interjection information 633, and syllable unit voice data 634.

Specifically, when the at least one voice data 612 and the text data 620 are input to the first model 721, the first model 721 may generate the word segment information 631 and the interjection information 633 by analyzing the at least one voice data 612, may divide the at least one voice data 612 into the syllable unit voice data 634 based on the word segment information 631, and may generate the rhythmical information 632, but the present disclosure is not limited thereto.

According to some embodiments of the present disclosure, the word segment information 631 may include information on at least one word that is included in the text data 620 and information on a time when the at least one word is spoken.

The information on the at least one word may include information on the word class of the word and information on the meaning of the word. In this case, an interjection may be excluded from the at least one word. That is, information that is obtained by analyzing at least one word that is included in a voice spoken by a user and that does not include an interjection may be obtained through the first model 721, but the present disclosure is not limited thereto.

The information on the time when the at least one word is spoken may include at least one of information indicating when a corresponding word is spoken compared to a total time and information indicating how long the user has spoken the corresponding word. In this case, the information indicating how long the user has spoken the corresponding word may be related to a speech rate, but the present disclosure is not limited thereto.

According to other some embodiments of the present disclosure, the word segment information 631 may include information on the number of words other than an interjection, information on the number of content words other than a redundant content word (e.g., nouns, verbs, adjectives, or adverbs), information on the number of postpositions (e.g., a subject case marker, an object case marker, or an adverbial case marker), information on the number of pre-final endings (e.g., subject enhancement, a tense, politeness, relative enhancement, calligraphy, or an emphasis) and final endings (e.g., termination or non-termination), information on the number of grammatical functional words (e.g., a postposition or the end of a word), information on the number of repetitions of a phoneme, syllable, word, a word segment, a phrase, or a sentence, information on the number of phonemic paraphasias, information on the number of semantic paraphasias, or information on the number of inversions, but the present disclosure is not limited thereto.

In the present disclosure, the rhythmical information may include information related to at least one of the strength and weakness of a sound, the rhythm of the sound, and the high and low of the sound when a user speaks at least one word. That is, the rhythmical information may include information related to a speaking method of a user, such as the high and low of a sound and the strength and weakness of the sound, but the present disclosure is not limited thereto.

In the present disclosure, the interjection information may include information on the type of at least one interjection included in the text data 620, a speech time of each of one or more interjections included in the text data 620, the number of repetitions of each of one or more interjections included in the text data 620, and a total repetition time of each of one or more interjections included in the text data 620. That is, the processor 110 may obtain information that is obtained by analyzing an interjection included in a voice spoken by a user through the first model 721, but the present disclosure is not limited thereto.

The information on the speech time of each of the one or more interjections may include at least one of information indicating when the interjection was spoken compared to a total time and information indicating how long the user has spoken the corresponding interjection. The information indicating how long the user has spoken the corresponding interjection may be related to a speech rate, but the present disclosure is not limited thereto.

In the present disclosure, the syllable unit voice data may mean that at least one voice data is divided in a syllable unit. For example, the syllable unit voice data may include voice data related to each of one or more words and voice data related to each of one or more interjections, but the present disclosure is not limited thereto.

The second output data 630 that is output by the first model 721 may include all of the word segment information 631, the rhythmical information 632, the interjection information 633, and the syllable unit voice data 634. The second output data 630 may include at least one of the word segment information 631, the rhythmical information 632, the interjection information 633, and the syllable unit voice data 634. However, in order to improve the accuracy of the cognitive function state identification model 700 of the present disclosure, it may be appropriate that the first model 721 generates all of the word segment information 631, the rhythmical information 632, the interjection information 633, and the syllable unit voice data 634.

The logic-based event processor 712 may extract linguistic feature information and voice feature information, based on the second output data that is output by the first model 721. Specifically, the logic-based event processor 712 may extract the linguistic feature information and the voice feature information by processing information having a form in which the second output data output by the first model 721 is continuous, but the present disclosure is not limited thereto.

In the present disclosure, the linguistic feature information may include information on frequency of use of at least one interjection (e.g., a word, such as "Oh!" or "Umm") and information relating to whether a preset word (e.g., a keyword (e.g., a center word or concept that must be spoken) or an analogue of a keyword) is included in at least one voice data. In this case, the information relating to whether the preset word is included may indicate information that includes the preset word compared to a total number of words. A degree in which the preset word is included may indicate the ratio of the preset word included compared to the total number of words, but the present disclosure is not limited to the example.

In the present disclosure, the voice feature information may include at least one of information on a total speech time that is taken for a user speaks, information on frequency that the user pauses while speaking compared to the total speech time, and information on a total time for which the user pauses while speaking compared to the total speech time. That is, the voice feature information may be information that is obtained by generally analyzing a time for which a user hesitates when speaking and a time that is taken for the user to think along with a total time that is taken for the user speaks, but the present disclosure is not limited to the example.

The linguistic feature information and the voice feature information that are output by the logic-based event processor 712 may be input to at least one model along with the user information, thus generating the first output data 650. In this case, the first output data 650 may include at least one of the predicted score value 651 and the cognitive state identification value 652.

The predicted score value 651 is a value which may be obtained when a user performs a cognitive ability test, and may mean a value that is obtained by predicting a cognitive impairment screening test (CIST) score of a user, for example. That is, the predicted score value 651 may mean a value that is obtained by predicting a test result score which may be obtained only when a user performs the CIST by using paper and a pencil, but the present disclosure is not limited thereto. The predicted score value 651 may include at least one of a CIST score and a mini-mental state examination (MMSE) score.

The cognitive state identification value 652 is a value related to a cognitive function state of a user, and may include at least one of a value of the probability that a user will be normal and a value of the probability that a cognitive function hindrance will be present, but the present disclosure is not limited thereto.

In the present disclosure, the processor 110 may determine a cognitive function state of a user based on the cognitive state identification value 652. Furthermore, the processor 110 may determine the intensity of a cognitive function state of a user based on the predicted score value 651.

Specifically, the processor 110 may divide a user into a normal group or a suspected cognitive decline group based on the category of the cognitive state identification value 652, and can correct final results more accurately based on the predicted score value 651. Moreover, the processor 110 may check the intensity of the normal or suspected cognitive decline group based on the predicted score value 651. That is, the two factors (i.e., the predicted score value 651 and the cognitive state identification value 652) that are included in the first output data 650 may complementarily act each other.

According to some embodiments of the present disclosure, the cognitive function state identification model may output only one of the predicted score value 651 and the cognitive state identification value 652 according to their usage, but the present disclosure is not limited thereto.

According to some embodiments of the present disclosure, at least one model may include at least one of the second model 722 for generating the predicted score value 651 and the third model 723 for generating the cognitive state identification value 652. In this case, the second model 722 may generate the predicted score value 651, based on linguistic feature information 641, voice feature information 642, and the user information 613. The third model 723 may generate the cognitive state identification value 652, based on the linguistic feature information 641, the voice feature information 642, and the user information 613. However, the present disclosure is not limited to such a case.

The first model 721, the second model 722, and the third model 723 may each be composed of a neural network, but the present disclosure is not limited thereto. The converter 711 and the logic-based event processor 712 may also be composed of a neural network.

In the present disclosure, a neural network may be composed of a set of interconnected computational units, which may generally be referred to as nodes. These nodes may also be referred to as neurons. The neural network may be configured to include at least one node. Nodes (or neurons) constituting the neural network may be interconnected by one or more links.

In the neural network, one or more nodes connected through a link may relatively form a relationship between an input node and an output node. The concepts of an input node and an output node are relative, and any node in an output node relationship with respect to one node may be in an input node relationship in a relationship with another node, and vice versa. As described above, an input node-to-output node relationship may be created around a link. One output node may be connected to one input node through a link, and vice versa.

In the relation between the input node and the output node connected through one link, a value of data of the output node may be determined based on data that is input to the input node. Here, the link interconnecting the input node and the output node may have a weight. The weight may be variable, and may be changed by a user or an algorithm so as for the neural network to perform a desired function. For example, when one or more input nodes are connected to one output node by each link, the output node may determine an output node value based on values that are input to input nodes connected to the output node and based on a weight set in a link corresponding to each input node.

As described above, in the neural network, one or more nodes may be interconnected through one or more links to form an input node and output node relationship in the neural network. The characteristics of the neural network may be determined according to the number of nodes and links in the dementia identification model, a correlation between nodes and links, and a weight value assigned to each of the links. For example, when there are two neural networks having the same number of nodes and links and different weight values between the links, the two neural networks may be recognized as different from each other.

The neural network may consist of a set of one or more nodes. A subset of nodes constituting the neural network may constitute a layer. Some of the nodes constituting the neural network may configure one layer based on distances from an initial input node. For example, a set of nodes having a distance of n from the initial input node may constitute n layers. The distance from the initial input node may be defined by the minimum number of links that should be traversed to reach the corresponding node from the initial input node. However, the definition of such a layer is arbitrary for the purpose of explanation, and the order of the layer in the neural network may be defined in a different way from that described above. For example, a layer of nodes may be defined by a distance from a final output node.

The initial input node may refer to one or more nodes to which data (i.e., at least one of the first information and the second information) is directly input without going through a link in a relationship with other nodes among nodes in the neural network. Alternatively, in a relationship between nodes based on a link in the neural network, it may mean nodes that do not have other input nodes connected by a link. Similarly, the final output node may refer to one or more nodes that do not have an output node in relation to other nodes among nodes in the neural network. In addition, a hidden node may refer to nodes constituting the neural network other than the first input node and the last output node.

According to some embodiments of the present disclosure, the first model 721, the second model 722, and the third model 723 may have a deep neural network structure.

A Deep Neural Network (DNN) may refer to a neural network including a plurality of hidden layers in addition to an input layer and an output layer. DNN may be used to identify the latent structures of data.

The DNN may include convolutional neural networks (CNNs), transformer network, Recurrent Neural Networks (RNNs), auto encoders, Generative Adversarial Networks (GANs), and a Restricted Boltzmann Machines (RBM), a Deep Belief Network (DBN), a Q network, a U network, a Siamese network, a Generative Adversarial Network (GAN), and the like. These DNNs are only provided as examples, and the present disclosure is not limited thereto.

In the present disclosure, a transformer network may be used for the first model 721. A deep neural network in which a recurrent neural network and a convolution neural network are combined may be used for the second model 722. Random Forest or CatBoost that uses a voting function may be used for the third model 723. However, the present disclosure is not limited to such examples.

According to some embodiments of the present disclosure, the plurality of models that are included in the cognitive function state identification model 700 may not be individually trained, but may be integrally trained. That is, the cognitive function state identification model 700 may be integrally trained to calculate at least one of the predicted score value 651 and the cognitive state identification value 652, when receiving the at least one voice data 612, the speech time information 611 related to the at least one voice data 612, and the user information 613. In this case, the cognitive function state identification model 700 may be trained in a way to update the weight of a neural network by back propagating a difference value between labeling data (e.g., at least one of a predicted score value for training and a cognitive state identification value for training) that has been labeled on data for learning (e.g., user information, at least one voice data, and speech time information related to the at least one voice data) and predicted data that is output by the cognitive function state identification model 700.

According to other some embodiments of the present disclosure, the plurality of models that are included in the cognitive function state identification model 700 may be individually trained and then combined.

Specifically, when receiving the text data 620 as input data, the first model 721 may be trained to output the second output data 630. When receiving the linguistic feature information 641, the voice feature information 642, and the user information 613, the second model 722 may be trained to output the predicted score value 651. When receiving the linguistic feature information 641, the voice feature information 642, and the user information 613, the third model 723 may be trained to output the cognitive state identification value 652. Furthermore, the cognitive function state identification model 700 may be generated by using the first model 721, the second model 722, and the third model 723 on which training has been completed.

Hereinafter, it is assumed and described that the cognitive function state identification model 700 is integrally trained for convenience of description, but the present disclosure is not limited thereto. After each of the plurality of models that are included in the cognitive function state identification model 700 is individually trained, the cognitive function state identification model 700 may be generated.

According to some embodiments of the present disclosure, the storage 120 of the device 100 may store a pre-learned cognitive function state identification model 700.

In the present disclosure, data for learning may be acquired through test users. In the present disclosure, the test users may include a user classified as a patient with mild cognitive impairment, a user classified as an Alzheimer's patient, a user classified as normal, and the like. However, the present disclosure is not limited thereto.

The cognitive function status identification model 700 of the present disclosure may be learned in a supervised learning manner. However, the present disclosure is not limited thereto, and the cognitive function status identification model may be learned in at least one manner of unsupervised learning, semi supervised learning, or reinforcement learning.

Learning of the cognitive function status identification model 700 may be a process of applying knowledge for performing an operation of identifying cognitive function status by the cognitive function status identification model 700 to a neural network.

The cognitive function status identification model 700 may be trained in a way that minimizes errors in output. Learning of the cognitive function status identification model 700 is a process of repeatedly inputting learning data (test result data for learning) into the cognitive function status identification model 700, calculating errors of an output (score value predicted through the neural network) and target (at least one of a predicted score value and a cognitive state identification value used as label data) of the dementia identification model on the learning data, and updating the weight of each node of the cognitive function status identification model 700 by back propagating the error of the cognitive function status identification model 700 from an output layer of the cognitive function status identification model 700 to an input layer in a direction of reducing the error.

A change amount of a connection weight of each node to be updated may be determined according to a learning rate. Calculation of the cognitive function status identification model 700 on the input data and back-propagation of errors may constitute a learning cycle (epoch). The learning rate may be differently applied depending on the number of repetitions of a learning cycle of the cognitive function status identification model 700. For example, in an early stage of learning the cognitive function status identification model 700, a high learning rate may be used to enable the cognitive function status identification model 700 to quickly acquire a certain level of performance, thereby increasing efficiency, and, in a late stage of learning the cognitive function status identification model 700, accuracy may be increased by using a low learning rate.

In the learning of the cognitive function status identification model 700, the learning data may be a subset of actual data (i.e., data to be processed using the learned cognitive function status identification model 700), and thus, there may be a learning cycle wherein errors for learning data decrease but errors for real data increase. Overfitting is a phenomenon wherein errors on actual data increase due to over-learning on learning data as described above.

The overfitting may act as a cause of increasing errors in a machine learning algorithm. To prevent such overfitting, methods such as increasing training data; regularization; and dropout that deactivate some of nodes in a network during a learning process, and utilization of a batch normalization layer may be applied.

According to some embodiments of the present disclosure, when the cognitive function state identification model 700 is trained, there may be a problem in which the training is not properly performed due to a data imbalance because the number of data on which a cognitive function hindrance has been labeled and the number of data that has been labeled as being normal are different from each other. Such a problem can be solved through over-sampling, that is, a method of extending the number of data on which a cognitive function hindrance has been labeled, that is, data having a minority category, so that the number of data on which a cognitive function hindrance has been labeled is matched with the number of data that has been labeled as being normal.

In the present disclosure, the over-sampling may be performed through a random over-sampling technique, a synthetic minority over-sampling technique (SMOTE), borderline-SMOTE, or an adaptive synthetic sampling (ADASYN) technique, but the present disclosure is not limited to the example.

If a data imbalance is solved through the over-sampling as described above, it could be seen that an area under the curve (AUC) is improved from 0.58 to 0.946. That is, it could be seen that classification performance of the model is greatly improved.

According to at least one of the aforementioned several embodiments of the present disclosure, the user's cognitive function status may be accurately diagnosed in a way that a patient rarely feels rejection.

In an embodiment of the present disclosure, the configurations and methods of the aforementioned several embodiments of the device 100 are not limitedly applied, and all or parts of each of the embodiments may be selectively combined to allow various modifications.

Various embodiments described in the present disclosure may be implemented in a computer or similar device-readable recording medium using, for example, software, hardware, or a combination thereof.

According to hardware implementation, some embodiments described herein may be implemented using at least one of application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, and other electrical units for performing functions. In some cases, some embodiments described in the present disclosure may be implemented with at least one processor.

The method of identifying cognitive function status by the at least one processor 110 of the device 100 using the cognitive function status identification model according to some embodiments of the present disclosure may be implemented as code readable by the at least one processor in a recording medium readable by the at least one processor 110 provided in the device 100. The at least one processor-readable recording medium includes all types of recording devices in which data readable by the at least one processor 110 is stored. Examples of the at least one processor-readable recording medium includes read only memory (ROM), random access memory (RAM), CD-ROM, a magnetic tape, a floppy disk, and an optical data storage device.

Although the present disclosure has been described with reference to the accompanying drawings, this is only an embodiment and the present disclosure is not limited to a specific embodiment. Various contents that can be modified by those of ordinary skill in the art to which the present disclosure belongs also belong to the scope of rights according to the claims. In addition, such modifications should not be understood separately from the technical spirit of the present disclosure.

What is claimed is:

1. A method of identifying, by at least one processor of a device, a cognitive function state of a user, the method comprising:
   inputting user information, at least one voice data, and speech time information related to the at least one voice data to a cognitive function state identification model; and
   identifying a cognitive function state of the user based on first output data that is output by the cognitive function state identification model,
   wherein the first output data comprises a cognitive state identification value comprising at least one of a value of a probability that the user is to be normal and a value of a probability that the user is to include a cognitive function hindrance, and a predicted score value that is obtained by predicting a score which is able to be obtained when the user performs a cognitive ability test, and
   the predicted score value is used when the cognitive function state is corrected and when an intensity of the cognitive function state is determined.

2. The method of claim 1, wherein the identifying of the cognitive function state of the user based on the first output data that is output by the cognitive function state identification model comprises:
   determining the cognitive function state of the user based on the cognitive state identification value; and
   determining the intensity of the cognitive function state of the user based on the predicted score value.

3. The method of claim 1, wherein the cognitive function state identification model comprises:
   a converter configured to convert the at least one voice data into text data based on the at least one voice data and the speech time information;
   a first model configured to generate second output data based on the text data;
   a logic-based event processor configured to extract linguistic feature information and voice feature information based on the second output data; and
   at least one model configured to generate the first output data, based on the linguistic feature information, the voice feature information, and the user information.

4. The method of claim 3, wherein the second output data comprises word segment information, rhythmical information, interjection information, and syllable unit voice data.

5. The method of claim 4, wherein the word segment information comprises information on at least one word included in the text data and information on a time when the at least one word is spoken.

6. The method of claim 5, wherein the rhythmical information comprises information related to at least one of a strength and weakness of a sound, a rhythm of the sound, and a high and low of the sound when the user speaks the at least one word.

7. The method of claim 4, wherein the interjection information comprises information on a type of each of one or more interjections included in the text data, a speech time of each of the one or more interjections, a number of repetitions of each of the one or more interjections, and a total repetition time of each of the one or more interjections.

8. The method of claim 7, wherein the linguistic feature information comprises information on frequency of use of the at least one interjection and information relating to whether a preset word is included in the at least one voice data.

9. The method of claim 3, wherein the voice feature information comprises at least one of information on a total speech time that is taken when the user speaks, information on frequency that the user pauses while speaking compared to the total speech time, and information on a total time for which the user pauses while speaking compared to the total speech time.

10. The method of claim 1, wherein the at least one voice data is obtained by using at least one of a method of obtaining first voice data and a method of obtaining second voice data, which is different from the method of obtaining the first voice data.

11. The method of claim 10, wherein the method of obtaining the first voice data comprises:
    performing a first task for obtaining a plurality of first voice data related to a plurality of images related to one story, respectively, while operating in conjunction with causing the plurality of images to be sequentially displayed in a user terminal one by one; and
    performing a second task for obtaining the second voice data while operating in conjunction with causing information on the one story to be displayed in the user terminal without displaying an image.

12. The method of claim 10, wherein the method of obtaining the second voice data comprises:
    performing a third task for causing a user terminal to display a first screen comprising a sentence;
    performing a fourth task for causing the user terminal to obtain an image comprising the user's eyes while operating in conjunction with displaying a moving object instead of the first screen; and
    performing a fifth task for causing the user terminal to obtain a recording file comprising the at least one voice data while operating in conjunction with displaying a second screen on which the sentence is hidden.

13. The method of claim 1, wherein the user information comprises at least one of information on an age and sex of the user and cognitive test result data of the user.

14. A computer program stored in a non-transitory computer-readable storage medium, wherein when being executed by at least one processor of a device, the computer program performs steps of identifying a cognitive function state of a user, the steps comprising:
    inputting user information, at least one voice data, and speech time information related to the at least one voice data to a cognitive function state identification model; and
    identifying a cognitive function state of the user based on first output data that is output by the cognitive function state identification model,
    wherein the first output data comprises a cognitive state identification value comprising at least one of a value of a probability that the user is to be normal and a value of a probability that the user is to include a cognitive function hindrance, and a predicted score value that is obtained by predicting a score which is able to be obtained when the user performs a cognitive ability test, and
    the predicted score value is used when the cognitive function state is corrected and when an intensity of the cognitive function state is determined.

15. A device for identifying a cognitive function state of a user, the device comprising:
    a storage unit configured to store at least one program instruction; and
    at least one processor configured to perform the at least one program instruction,
    wherein the at least one processor is configured to:
    input user information, at least one voice data, and speech time information related to the at least one voice data to a cognitive function state identification model, and
    identify a cognitive function state of the user based on first output data that is output by the cognitive function state identification model,
    wherein the first output data comprises a cognitive state identification value comprising at least one of a value of a probability that the user is to be normal and a value of a probability that the user is to include a cognitive function hindrance, and a predicted score value that is obtained by predicting a score which is able to be obtained when the user performs a cognitive ability test, and
    the predicted score value is used when the cognitive function state is corrected and when an intensity of the cognitive function state is determined.

\* \* \* \* \*